United States Patent [19]
Rampal

[11] Patent Number: 5,985,567
[45] Date of Patent: Nov. 16, 1999

[54] HYBRIDIZATION DETECTION BY PRETREATING BOUND SINGLE-STRANDED PROBES

[75] Inventor: Jang B. Rampal, Yorba Linda, Calif.

[73] Assignee: Beckman Coulter, Inc., Fullerton, Calif.

[21] Appl. No.: 08/912,154

[22] Filed: Aug. 15, 1997

[51] Int. Cl.[6] .................................................. C12Q 1/68
[52] U.S. Cl. .............................................. 435/6; 422/104
[58] Field of Search ................................... 422/101, 104; 436/518; 435/6, 287, 180, 810

[56] References Cited

U.S. PATENT DOCUMENTS

| | | | |
|---|---|---|---|
| 5,268,268 | 12/1993 | Snisky et al. | 435/6 |
| 5,429,807 | 7/1995 | Matson et al. | 422/131 |
| 5,512,436 | 4/1996 | Stone | 435/6 |
| 5,554,501 | 9/1996 | Coassin et al. | 435/6 |
| 5,583,211 | 12/1996 | Coassin et al. | 536/23.1 |
| 5,620,847 | 4/1997 | Greisen et al. | 435/6 |
| 5,665,548 | 9/1997 | Erlich et al. | 435/6 |
| 5,837,832 | 11/1998 | Chee et al. | 536/22.1 |

OTHER PUBLICATIONS

Wohl, et al (1995) Electrophoresis, vol. 16, pp. 739–741.
Sambrook (1989)Molecular Cloning A Laboratory Manual, Cold Spring Harbor Laboratory Press, 9.47–9.58.
Breslauer, Kenneth J., et al., "Predicting DNA Duplex Stability Form the Base Sequence", *Proc. Natl. Acad. Sci., USA*, vol. 83 (Jun. 1986), pp. 3746–3750.
Lee, Che–Hung et al., "Unwinding of Double–Stranded DNA Helix by Dehydration," *Proc. Natl. Acad. Sci., (USA)*, vol. 78, No. 5 (May 1981), pp. 2838–2842.
Lee, Jeremy S., "The Stability of Polypurine Tetraplexes in the Presence of Mono– and Divalent Cations", *Nucleic Acids Research*, vol. 18, No. 20 (1990), pp. 6057–6060, Oxford University Press.
Levine, Lawrence, et al., "The Relationship of Structure to the Effectiveness of Denaturing Agents for Deoxyribonucleic Acid," *Biochemistry*, vol. 2, No. 1 (Jan.–Feb. 1963), pp. 168–175.

Matson, Robert S., et al., "Biopolymer Synthesis on Polypropylene Supports", *Analytic Biochemistry*, vol. 217 (1994), pp. 306–310, Academic Press, Inc.
Matson, Robert S., "Polymer Synthesis on Polypropylene Supports: Oligonucleotide Arrays," *Analytic Biochemistry*, vol. 224 (1995), pp. 110–116, Academic Press, Inc.
Matthews, Jayne A., et al., "Analytic Strategies for the Use of DNA Probes," *Analytic Biochemistry*, vol. 169 (1988), pp. 1–25, Academic Press, Inc.
Niklforov, Theo T., et al., "Genetic Bit Analysis: a Solid Phase Method for Typing Single Nucleotide Polymorphisms," *Nucleic Acids Research*, vol. 22, No. 20 (1994), pp. 4167–4175, Oxford University Press.
Wehnert, Manfred S., et al., "A Rapid Scanning Strip for Tri– and Dinucleotide Short Tandem Repeats," *Nucleic Acids Research*, vol. 22, No. 9 (1994), pp. 7101–7104, Oxford University Press.
Wolfe, Alan R., et al, "The Effect of Sodium Ion Concentration on Intrastrand Base–Pairing in Single–Stranded DNA", *Nucleic Acids Research*, vol. 22, No. 15 (1994), pp. 3147–3150, Oxford University Press.

*Primary Examiner*—Kenneth R. Horlick
*Attorney, Agent, or Firm*—William H. May; Margaret A. Kivinski; Sheldon & Mak

[57] ABSTRACT

An improved method for detecting hybridized biomolecules is provided which comprises the steps of, providing a plurality of probe biomolecules on a solid support surface; pre-treating the plurality of probe biomolecules with an effective amount of a pre-treatment solution to produce a signal having an increased intensity of at least two (2) times, as compared to an identical detection method that does not include the pre-treating step; applying a buffer solution to the probe biomolecules; hybridizing the probe biomolecules with a plurality of target biomolecules to form a hybridized complex; and, developing and detecting the signal intensity. The developing step of the method may further include the steps of, treating the hybridized complex with a conjugating solution, and treating the conjugated, hybridized complex with a detection reagent.

26 Claims, 14 Drawing Sheets

|     | 1 | 2 | 3 | 4 | 5 | 6 | 7 | 8 | 9 | 10 | 11 | 12 | 13 | 14 | 15 | 16 | 17 | 18 |
|-----|---|---|---|---|---|---|---|---|---|----|----|----|----|----|----|----|----|----|
| 1   | A | A | A | A | A | A | A | A | A | A  | A  | A  | A  | A  | A  | A  | A  | A  |
| 2   | A | A | A | A | A | A | A | A | A | A  | A  | A  | A  | A  | A  | A  | A  | A  |
| 3   | C | G | G | G | T | G | T | G | G | C  | G  | G  | C  | C  | G  | C  | G  | G  |
| 4   | C | G | G | G | T | G | T | G | G | C  | G  | G  | C  | C  | G  | C  | G  | G  |
| 5   | G | G | G | T | G | T | G | G | C | G  | G  | C  | C  | G  | C  | G  | G  |    |
| 6   | G | G | G | T | G | T | G | G | C | G  | G  | C  | C  | G  | C  | G  | G  |    |
| 7   | C | G | G | G | T | G | T | G | G | C  | G  | G  | C  | C  | G  | C  | C  |    |
| 8   | C | G | G | G | T | G | T | G | G | C  | G  | G  | C  | C  | G  | C  | G  |    |
| 9   | G | G | G | T | G | T | G | G | C | G  | G  | C  | C  | G  | C  | G  |    |    |
| 10  | G | G | G | T | G | T | G | G | C | G  | G  | C  | C  | G  | C  | G  |    |    |
| 11  | G | G | T | G | T | G | G | C | G | G  | C  | C  | G  | C  | G  | G  |    |    |
| 12  | G | G | T | G | T | G | G | C | G | G  | C  | C  | G  | C  | G  | G  |    |    |
| 13  | C | G | G | G | T | G | T | G | G | C  | G  | G  | C  | C  | G  | C  |    |    |
| 14  | C | G | G | G | T | G | T | G | G | C  | G  | G  | C  | C  | G  | C  |    |    |
| 15  | G | G | G | T | G | T | G | G | C | G  | G  | C  | C  | G  | C  |    |    |    |
| 16  | G | G | G | T | G | T | G | G | C | G  | G  | C  | C  | G  | C  |    |    |    |
| 17  | G | G | T | G | T | G | G | C | G | G  | C  | C  | G  | C  | G  |    |    |    |
| 18  | G | G | T | G | T | G | G | C | G | G  | C  | C  | G  | C  | G  |    |    |    |
| 19  | G | T | G | T | G | G | C | G | G | C  | C  | G  | C  | G  | G  |    |    |    |
| 20  | G | T | G | T | G | G | C | G | G | C  | C  | G  | C  | G  | G  |    |    |    |
| 21  | C | G | G | G | T | G | T | G | G | C  | G  | G  | C  | C  | G  |    |    |    |
| 22  | C | G | G | G | T | G | T | G | G | C  | G  | G  | C  | C  | G  |    |    |    |
| 23  | G | G | T | G | T | G | G | C | G | G  | C  | C  | G  | C  |    |    |    |    |
| 24  | G | G | T | G | T | G | G | C | G | G  | C  | C  | G  | C  |    |    |    |    |
| 25  | G | T | G | T | G | G | C | G | G | C  | C  | G  | C  | G  |    |    |    |    |
| 26  | G | T | G | T | G | G | C | G | G | C  | C  | G  | C  | G  |    |    |    |    |
| 27  | G | G | G | T | G | T | G | G | C | G  | G  | C  | C  | G  |    |    |    |    |
| 28  | G | G | G | T | G | T | G | G | C | G  | G  | C  | C  | G  |    |    |    |    |
| 29  | G | G | T | G | T | G | G | C | G | G  | C  | C  | G  |    |    |    |    |    |
| 30  | G | G | T | G | T | G | G | C | G | G  | C  | C  | G  |    |    |    |    |    |
| 31  | G | T | G | T | G | G | C | G | G | C  | C  | G  | C  |    |    |    |    |    |
| 32  | G | T | G | T | G | G | C | G | G | C  | C  | G  | C  |    |    |    |    |    |
| 33  | G | T | G | T | G | G | C | G | G | C  | C  | G  |    |    |    |    |    |    |
| 34  | G | T | G | T | G | G | C | G | G | C  | C  | G  |    |    |    |    |    |    |
| 35  | T | G | T | G | G | C | G | G | C | C  | G  | C  |    |    |    |    |    |    |
| 36  | T | G | T | G | G | C | G | G | C | C  | G  | C  |    |    |    |    |    |    |
| 37  | T | G | T | G | G | C | G | G | C | C  | G  |    |    |    |    |    |    |    |
| 38  | T | G | T | G | G | C | G | G | C | C  | G  |    |    |    |    |    |    |    |
| 39  | T | G | T | G | G | C | G | G | C | C  |    |    |    |    |    |    |    |    |
| 40  | T | G | T | G | G | C | G | G | C | C  |    |    |    |    |    |    |    |    |
| 41  | A | A | A | A | A | A | A | A | A | A  | A  | A  | A  | A  | A  | A  | A  |    |
| 42  | C | G | G | G | T | G | T | G | G | C  | T  | G  | C  | C  | G  | C  | G  | A  |
| 43  | C | G | G | G | T | G | T | G | G | C  | T  | G  | C  | C  | G  | C  | G  | G  |
| 44  | G | G | G | T | G | T | G | G | C | T  | G  | C  | C  | G  | C  | G  | G  |    |
| 45  | G | G | T | G | T | G | G | C | T | G  | C  | C  | G  | C  | G  | G  |    |    |
| 46  | G | T | G | T | G | G | C | T | G | C  | C  | G  | C  | G  | G  |    |    |    |
| 47  | T | G | T | G | G | C | T | G | C | C  | G  | C  | G  | G  |    |    |    |    |
| 48  | G | T | G | T | G | G | C | T | G | C  | C  | G  | C  | G  |    |    |    |    |
| 49  | T | G | T | G | G | C | T | G | C | C  | G  | C  | G  |    |    |    |    |    |
| 50  | G | T | G | T | G | G | C | T | G | C  | C  | G  | C  |    |    |    |    |    |
| 51  | G | T | G | G | C | T | G | C | C | G  | C  | G  | G  |    |    |    |    |    |
| 52  | G | T | G | G | C | T | G | C | C | G  | C  | G  | G  |    |    |    |    |    |
| 53  | G | T | G | G | C | T | G | C | C | G  | C  | G  | G  |    |    |    |    |    |
| 54  | T | G | G | C | T | G | C | C | G | C  | G  | G  |    |    |    |    |    |    |
| 55  | T | G | G | C | T | G | C | C | G | C  | G  | G  |    |    |    |    |    |    |
| 56  | T | G | G | C | T | G | C | C | G | C  | G  |    |    |    |    |    |    |    |
| 57  | T | G | G | C | T | G | C | C | G | C  |    |    |    |    |    |    |    |    |
| 58  | G | T | G | T | G | G | C | T | G | C  | C  | G  |    |    |    |    |    |    |
| 59  | G | T | G | G | C | T | G | C | C | G  | C  | G  |    |    |    |    |    |    |
| 60  | T | G | G | C | T | G | C | C | G | C  |    |    |    |    |    |    |    |    |
| 61  | G | T | G | G | C | T | G | C | C | G  | C  |    |    |    |    |    |    |    |
| 62  | T | G | G | C | T | G | C | C | G | C  |    |    |    |    |    |    |    |    |
| 63  | G | T | G | G | C | T | G | C | C | G  |    |    |    |    |    |    |    |    |
| 64  | A | A | A | A | A | A | A | A | A | A  | A  | A  | A  | A  | A  | A  | A  |    |
| 65  |   |   |   |   |   |   |   |   |   |    |    |    |    |    |    |    |    |    |
| 66  |   |   |   |   |   |   |   |   |   |    |    |    |    |    |    |    |    |    |
| 67  |   |   |   |   |   |   |   |   |   |    |    |    |    |    |    |    |    |    |
| 68  |   |   |   |   |   |   |   |   |   |    |    |    |    |    |    |    |    |    |
| 69  |   |   |   |   |   |   |   |   |   |    |    |    |    |    |    |    |    |    |

17 F Spreadsheet

FIG. 3

Hot Water - 95°C Hybridization with PCR Target control 95C/5min

Panel: 17F H-ras
Target: 63 base pair PCR

HYBRIDIZATION DETECTION BY PRETREATING BOUND SINGLE-STRANDED PROBES

BACKGROUND

The present invention is directed to an improved method for detecting hybridized biomolecules, such as deoxyribonucleic acid (DNA), in solid phase hybridization. The improved method results in increased hybridization signal intensities in the analysis of biomolecules.

In the analysis of biomolecules using a solid phase, a plurality of probe biomolecules may be attached to a solid polymeric matrix or substrate in a pre-determined format referred to as an array. During hybridization, the probe biomolecules are subjected to treatment with complementary target biomolecules to form hybrid duplexes or complexes. Areas of the array where duplexes or complexes form are then detected by known detection techniques.

Known hybridization techniques used in solid-phase hybridization include the Southern blotting technique, also known as the forward-blot technique, and the reverse Southern blotting technique. The Southern blotting technique allows for the mapping of a position of a DNA sequence relative to restriction enzyme sites. In the Southern blotting technique, target biomolecules are initially attached to a solid support substrate, and then the target biomolecules are treated with probe biomolecules and undergo hybridization with the probe biomolecules.

In the reverse Southern blotting technique, pre-synthesized probe biomolecules are initially attached to a solid support substrate, and then the probe biomolecules are treated with target biomolecules and undergo hybridization with the target biomolecules. The reverse Southern blotting technique does not limit the number of target biomolecules that may be used and allows for a high throughput, that is, a large volume of data may be collected in a short period of time.

Under ideal conditions, immobilized probe biomolecules should be easily accessible for hybridization with target molecules. However, under less than ideal conditions, hybridization between the probe biomolecules and the target biomolecules is often inhibited or prevented because the probe biomolecules in the array are not available for interaction with the target biomolecules. This unavailability can occur when the probe biomolecules which are initially attached to the solid support surface form duplexes or complexes with themselves or self-hybridize upon themselves, by folding back on themselves to form hairpin loop secondary structures. Such secondary structures are referred to as intra-strand interactions. The unavailability of the probe biomolecules for hybridization with the target biomolecules can also occur when the probe biomolecules hybridize with adjacent probe biomolecules on the array surface to form secondary structure attachments referred to as inter-strand interactions. The presence of intra-strand and inter-strand secondary structures on the probe biomolecules retards the process of hybridization with target biomolecules.

A known method of enhancing hybridization of complementary polynucleotides in a buffered aqueous medium under hybridization conditions is disclosed in U.S. Pat. No. 5,512,436 to Stone. Such method is concerned with increasing the rate of hybridization and includes the use of a blocking agent.

There is a need for an improved method in solid phase array analysis for detection of biomolecules that results in an increased occurrence of hybridization between the probe biomolecules and the target biomolecules, that minimizes the formation of inter-strand and intra-strand interactions on the probe biomolecules, and that results in an increased hybridization signal intensity.

SUMMARY OF THE INVENTION

The present invention meets this need by providing an improved method for detecting hybridized biomolecules in solid phase arrays. The present invention provides an improved method that enhances hybridization between the probe biomolecules and the complementary target biomolecules and, in turn, increases or enhances the hybridization signal intensity. The present invention further provides an improved method that increases the sensitivity of the signal intensity, and thus provides greater information in the analysis of genetic sequences. It is believed that the improved method minimizes the formation of inter-strand and intra-strand interactions on the probe biomolecules and renders the probe biomolecules available for hybridization with the complementary target biomolecules.

Thus, the method of the present invention has the advantages of increasing the occurrence of hybridization between the probe biomolecules and the target biomolecules and of enhancing the hybridization signal intensity. In addition, the present invention has the advantage of providing a less costly method since relatively less target sample is needed. In addition, the method of the present invention has the advantage of increasing and improving the sensitivity of the signal intensity.

The method of the present invention may have applications in the areas of genetic analysis, biomolecular diagnostics, sequencing by hybridization, molecular biology, and in other related fields.

In the preferred version of the present invention, an improved method for detecting hybridized biomolecules is provided which comprises the steps of, providing a plurality of probe biomolecules on a solid support surface; pre-treating the plurality of probe biomolecules with an effective amount of a pre-treatment solution to produce a signal having an increased intensity of at least two (2) times, as compared to an identical detection method that does not include the pre-treating step; applying a buffer solution to the probe biomolecules; hybridizing the probe biomolecules with a plurality of target biomolecules to form a hybridized complex; and, developing and detecting the signal intensity.

The developing step of the method may further include the steps of, treating the hybridized complex with a conjugating solution, and treating the conjugated, hybridized complex with a detection reagent.

The probe biomolecule preferably comprises deoxyribonucleic acid, ribonucleic acid, or peptide-nucleic acid. The solid support surface preferably comprises polypropylene. The target biomolecule preferably comprises deoxyribonucleic acid, ribonucleic acid, peptide-nucleic acid, or polymerase chain reaction fragments. The pre-treating step is preferably carried out at a temperature in the range of about 20 degrees C. to about 30 degrees C., and for an effective period of time in the range of about 1 minute to about 60 minutes.

The pre-treatment solution may include solutions that comprise organic compounds, solutions that comprise inorganic compounds, or hot (boiling) water. The pre-treatment solution comprising organic compounds preferably comprises denaturants and organic acids. The organic denaturants may comprise formamide; dimethyl formamide; urea;

guanidinium hydrochloride; guanidinium thiocyanate; guanidinium isocyanate; spermine; spermidine; glyoxal; alcohols; or 1,1,3,3-tetramethyl urea. The solution of denaturant may further comprise sodium dodecyl sulfate (SDS), ethylenediaminetetra-acetic acid (EDTA), or a mixture thereof. The organic acid pre-treatment solution may comprise acetic acid, formic acid, trifluoroacetic acid, or trichloroacetic acid.

The pre-treatment solution comprising inorganic compounds preferably comprises aqueous solutions of bases, salts, and inorganic acids. The aqueous solution of base may comprise sodium hydroxide, lithium hydroxide, sodium carbonate, sodium bicarbonate, or methyl mercuric hydroxide. The aqueous solution of base may further comprise sodium dodecyl sulfate (SDS), ethylenediaminetetra-acetic acid (EDTA), or a mixture thereof. The preferred aqueous solution of base comprises sodium hydroxide (NaOH) having a concentration of less than about 10 molar.

The aqueous solution of salt may comprise sodium chloride, potassium chloride, lithium chloride, sodium acetate, sodium citrate, sodium phosphate, magnesium chloride, manganese chloride, cesium chloride, barium chloride, or sodium dodecyl sulfate. The preferred aqueous solution of inorganic acids may comprise hydrochloric acid (HCl) having a concentration of less than about 1 N (Normal).

In another version of the present invention, an improved method for detecting hybridized biomolecules is provided in which the pre-treating step includes a pre-treatment solution of hot (boiling) water having a temperature in the range of about 90 degrees C. to about 97 degrees C. The probe biomolecules are pre-treated for an effective period of time in the range of about 30 seconds to about 45 minutes, to produce a signal having an increased intensity of at least two (2) times, as compared to an identical detection method that does not include the pre-treating step.

In another version of the present invention, a kit for detecting hybridized biomolecules is provided comprising, a) a plurality of probe biomolecules on a solid polypropylene support surface; b) an effective amount of a pre-treatment solution for application to the probe biomolecules to produce a signal of interest having an increased intensity of at least two (2) times, as compared to probe biomolecules that are not pre-treated with the pre-treatment solution; c) a buffer solution; d) a plurality of target biomolecules for hybridization with the probe biomolecules to form a hybridized complex; e) a conjugating solution for developing the signal of interest; and, f) a detection reagent for detecting the signal of interest.

DESCRIPTION OF THE DRAWINGS

These and other features, aspects and advantages of the present invention will become better understood from the following description of the drawings, detailed description of the invention, appended claims, and accompanying drawings, where:

FIG. 3 illustrates a typical array panel spread sheet (17F) used to obtain information in the Examples set forth below using the method of the present invention;

DETAILED DESCRIPTION

The following description of the preferred embodiments of the invention is merely exemplary in nature and is not intended to limit the invention or its applications or uses.

According to one aspect of the present invention, there is provided an improved method for detecting hybridized biomolecules comprising the steps of, providing a plurality of probe biomolecules on a solid support surface; pre-treating the plurality of probe biomolecules with an effective amount of a pre-treatment solution to produce a signal having an increased intensity of at least two (2) times, as compared to an identical detection method that does not include the pre-treating step; applying a buffer solution to the probe biomolecules; hybridizing the probe biomolecules with a plurality of target biomolecules to form a hybridized complex; and, developing and detecting the signal intensity.

Figure 1:
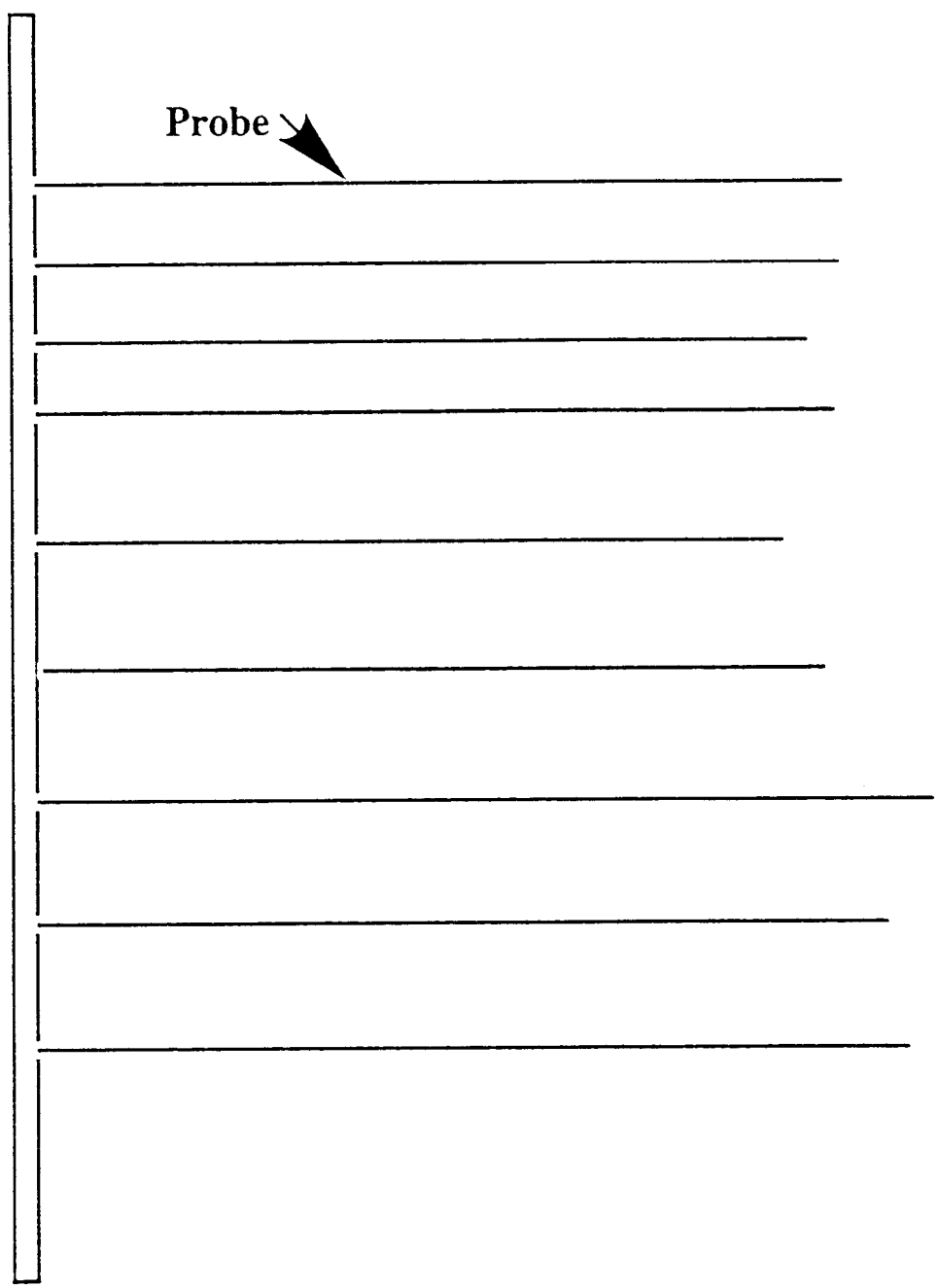
FIG. 1 illustrates a model of an ideal array of probe biomolecules attached to a solid support, in which the probe biomolecules are freely available for hybridization with target biomolecules.
Figure 2:
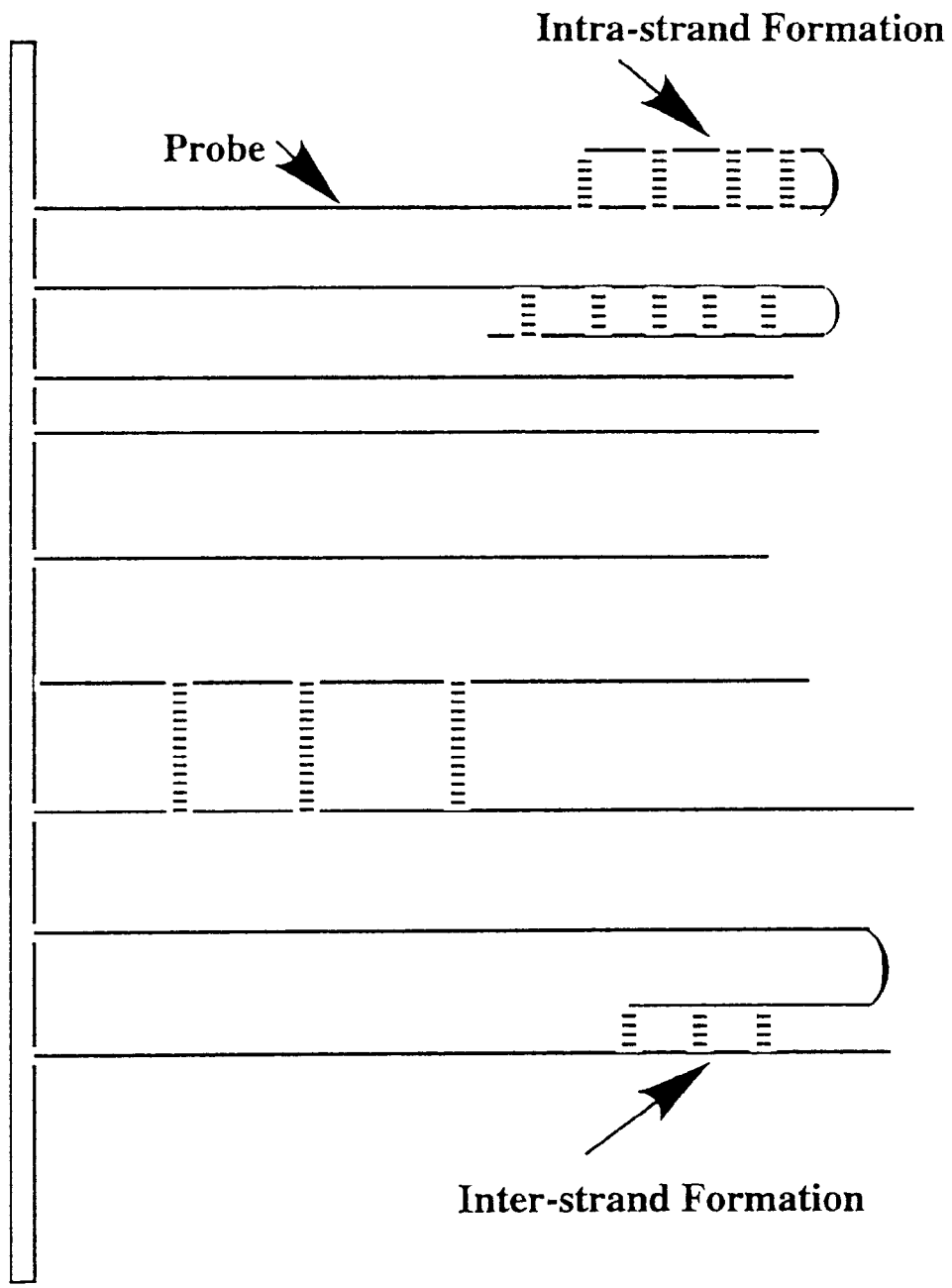
FIG. 2 illustrates a model of an array of probe biomolecules attached to a solid support, in which the probe biomolecules have intra-strand and inter-strand secondary structure formations.

FIG. 1 illustrates a model of an ideal array in which probe biomolecules are attached to a solid support, and in which the probe biomolecules are freely available for hybridization with target biomolecules. FIG. 2 illustrates a model of an array of probe biomolecules attached to a solid support, in which the probe biomolecules have formed intra-strand and inter-strand secondary structures. The present invention provides an improved method that enhances hybridization between the probe biomolecules and the complementary target biomolecules and that, in turn, increases or enhances the hybridization signal intensity. It is believed that the method of the present invention minimizes the formation of intra-strand and inter-strand secondary structure formations by the probe biomolecules, thus rendering the probe biomolecules in the array available for hybridization with complementary target biomolecules.

The first step in the method is providing a plurality of probe biomolecules on a solid support surface. For purposes of this application, the term "probe biomolecule" means biological or chemical components that are attached to the surface of a solid support substrate, such as a polypropylene substrate. Suitable probe biomolecules may include oligonucleotides, proteins, peptides, oligosaccharides, lipids, phospholipids, avidin, nucleic acids, analogues of the foregoing, and combinations of at least two of the foregoing. For purposes of this application, the term "analogues" means natural and synthetic variants of the selected biomolecule. Preferably, the probe biomolecule is an oligonucleotide such as deoxyribonucleic acid (DNA), ribonucleic acid (RNA), or peptide-nucleic acid (PNA). More preferably, the probe biomolecule is DNA. The biomolecular synthesis of the present invention is preferably accomplished by synthesizing the oligonucleotides directly onto a polymeric matrix surface or solid support surface. The solid phase synthesis of biomolecules requires a solid support surface to which the probe biomolecules are attached. The plurality of probe biomolecules may be attached to the solid support surface in a pre-determined format referred to as an array. A device for creating biomolecule arrays on a solid support surface, such as may be used to create the arrays in the present invention, is disclosed in U.S. Pat. No. 5,429,807, to Matson et al., which has been assigned to the assignee of the present application, and which is herein incorporated by reference. Automated biomolecular synthesis may be carried out with the Oligo 1000 DNA Synthesizer developed by Beckman Instruments, Inc. Binary-Pak phosphoramidite and other synthesis reagents may also be obtained from Beckman Instruments, Inc. Both cleavable and noncleavable linked oligonucleotides may be synthesized depending upon the application desired.

The solid support surface used in the method of the present invention is formed from a suitable material including, polypropylene, polyethylene, polybutylene, polyisobutylene, polybutadiene, polyisoprene, polyvinylpyrrolidine, polytetrafluoroethylene, polyvinylidene difluoride, polyfluoroethylene-propylene, polyethylenevinyl alcohol, polymethylpentene, polychlorotrifluoroethylene, polysulfones, hydroxylated biaxially oriented polypropylene, aminated biaxially oriented polypropylene, thiolated biaxially oriented polypropylene, ethyleneacrylic acid, ethylene methacrylic acid, and blends of copolymers thereof.

In general, suitable characteristics of the material that may be used to form the solid support surface include, amenability to surface activation such that upon activation, the surface of the support is capable of covalently attaching biomolecules thereto; amenabilty to "in situ" (in place) synthesis of biomolecules; being chemically inert, such that at the termination of biomolecular synthesis, areas on the support not occupied by the biomolecules are not amenable to non-specific binding, or when such non-specific binding does occur, such materials can be readily removed from the surface without removal of the biomolecules; and easy handling and manipulation such that the material may be used in various applications.

The preferred solid support surface is polypropylene. Polypropylene is chemically inert and hydrophobic. Because polypropylene is chemically inert, problems associated with non-specific binding are substantially avoided such that detection sensitivity is significantly improved. For example, polypropylene has good chemical resistance to a variety of organic acids (i.e., formic acid, acetic acid, and the like), organic agents (i.e., acetone, ethyl alcohol, acetonitrile, and the like), bases (i.e., sodium hydroxide, ammonium hydroxide, and the like), salts (i.e., sodium chloride, lithium chloride, and the like), oxidizing agents (i.e., peracetic acid, iodine solutions, and the like), and mineral acids (i.e., hydrochloric acid, and the like). In addition, polypropylene provides a low fluorescence background. This minimizes background interference, and thus increases the sensitivity of a signal of interest.

A particularly preferred surface activated organic polymer is a polypropylene material aminated via radio frequency plasma discharge. Such materials are preferably utilized for the in-situ attachment of nucleotides and/or amino acids thereto, and thus are particularly well suited for the synthesis of oligonucleotides. The amine groups on the activated organic polymers are reactive with nucleotides such that the nucleotides and/or amino acids introduced thereto are covalently attached onto the surface of the polymer. In certain preferred embodiments, the polypropylene is in the form of a biaxially oriented film, such as the biaxially oriented polypropylene film disclosed in U.S. Pat. No. 5,554,501, to Coassin et al., which has been assigned to the assignee of the present application, Beckman Instruments, Inc., and which is herein incorporated by reference. The polypropylene used with the present invention may also be in the form of threads, beads, or sheets.

In the present invention, the polypropylene film preferably has the dimensions of about 8 cm (centimeters) in length by about 8 cm in width and has a nominal thickness of about 0.00254 cm. The density of the polypropylene film used is approximately 5–6 pico mole per $mm^2$ (millimeter). The polypropylene film may be obtained from Catalina Plastics of Calabasas, Calif. The polypropylene film may also be aminated using radiofrequency plasma discharge in the presence of anhydrous ammonia, such as with a plasma generator Model PS0150E, obtained from Plasma Sciences of Foster City, Calif. Preferably, the polypropylene film is placed over a block having 64 separated channels on it. The film may be cut into array strips. A typical array strip used in the present invention may have the dimensions of 7 cm in length by 0.5 cm in width. In another embodiment, the polypropylene film may include attached pre-synthesized probes. For purposes of the present invention, the number of bases on the array is preferably in the range of about 8 bases to about 50 bases. Bases may also be referred to as "mer", i.e., 17 mer=17 bases. More preferably, in the present invention, the length of bases is in the range of about 10 bases to about 24 bases. Most preferably, the length of bases is in the range of about 12 bases to about 18 bases. This range of base length has been found to be very stable under hybridization conditions. Under hybridization conditions at ambient or room temperature, with a probe length of 10–24 bases, the signal intensity may be clearly seen, whereas, with a shorter probe length (8 bases and lower) under hybridization conditions at ambient or room temperature, the signal intensity may not be clearly seen. However, at temperatures substantially below ambient or room temperature, i.e., zero (0) degrees C. to about eight (8) degrees C., a shorter probe length (8 bases and lower), is preferred. At such lower temperatures, such shorter probe length has been found to be more stable under hybridization conditions.

The second step of this aspect of the method of the present invention is pre-treating the plurality of probe biomolecules with a pre-treatment solution. The pre-treatment solution may include solutions that comprise organic compounds, solutions that comprise inorganic compounds, or hot (boiling) water. The pre-treatment solution comprising organic compounds preferably comprises denaturants and organic acids. The preferred organic denaturants may comprise formamide; dimethyl formamide; urea; guanidinium hydrochloride; guanidinium thiocyanate; guanidinium isocyanate; spermine; spermidine; glyoxal; alcohols; or 1,1,3,3-tetramethyl urea. However, other suitable organic denaturants may also be used. The solution comprising the denaturant may further comprise sodium dodecyl sulfate (SDS), preferably 0.01% SDS; ethylenediaminetetra-acetic acid (EDTA), preferably 10 millimolar EDTA; or a mixture of SDS and EDTA. Most preferably, the pre-treatment solution of denaturant is formamide having a concentration in the range of about 40% to about 100%, wherein the formamide having a concentration of less than 100% is in sodium dodecyl sulfate solution.

The preferred organic acid pre-treatment solution used in the method of the present invention may comprise acetic acid, formic acid, trifluoroacetic acid, or trichloroacetic acid. However, other suitable organic acids may also be used. The solution comprising the organic acid may further comprise sodium dodecyl sulfate (SDS), preferably 0.01% SDS; ethylenediaminetetra-acetic acid (EDTA), preferably 10 millimolar EDTA; or a mixture thereof The pre-treatment solution comprising inorganic compounds preferably comprises aqueous solutions of bases, salts, or inorganic acids. The aqueous solution of base may comprise sodium hydroxide, lithium hydroxide, sodium carbonate, sodium bicarbonate, or methyl mercuric hydroxide. However, other suitable bases may also be used. The aqueous solution of base may further comprise, in solution, sodium dodecyl sulfate (SDS), preferably 0.01% SDS; ethylenediaminetetra-acetic acid (EDTA), preferably 10 millimolar EDTA; or a mixture thereof. In particular, sodium hydroxide (NaOH) in solution demonstrates excellent results with the method of the present invention. The preferred aqueous solution of base comprises sodium hydroxide (NaOH) having a concentration of less than about 10 molar. The more preferred aqueous solution of base comprises sodium hydroxide having a concentration of less than about 10 molar in ethylenediaminetetra-acetic acid (EDTA) in sodium dodecyl sulfate (SDS). The most preferred aqueous solution of base is sodium hydroxide having a concentration of about 1.0 molar, in 10 millimolar ethylenediaminetetra-acetic acid (EDTA) in 0.01% sodium dodecyl sulfate (SDS).

The preferred aqueous solution of salt may comprise sodium chloride, potassium chloride, lithium chloride, sodium acetate, sodium citrate, sodium phosphate, magnesium chloride, manganese chloride, cesium chloride, barium chloride, or sodium dodecyl sulfate. However, other suitable inorganic salts may also be used. The aqueous solution of salt may further comprise, in solution, sodium dodecyl sulfate (SDS), preferably 0.01% SDS; ethylenediaminetetra-acetic acid (EDTA), preferably 10 millimolar EDTA; or a mixture thereof.

The preferred aqueous solution of inorganic acid comprises hydrochloric acid (HCl). Preferably, the concentration of the hydrochloric acid used is less than about 1 N (Normal). However, other suitable inorganic acids may also be used. The aqueous solution of inorganic acid may further comprise, in solution, sodium dodecyl sulfate (SDS), preferably 0.01% SDS; ethylenediaminetetra-acetic acid (EDTA), preferably 10 millimolar EDTA; or a mixture thereof. The pre-treatment solution of the method of the present invention may also comprise hot (boiling) water having a temperature in the range of about 90 degrees C. to about 97 degrees C. The use of hot (boiling) water heated to a temperature in this temperature range demonstrates an increase in hybridization signal intensity.

For purposes of this invention, the amount of pre-treatment solution used in the method is an effective amount to produce an increased hybridization signal intensity and depends on the pre-treatment solution that is selected. Preferably, the pre-treatment solution is prepared in about 100 microliters ($\mu l$) of solution. For purposes of this invention, the length of time over which the probe biomolecules are pre-treated with a selected pre-treatment solution is for an effective period of time to produce an increased hybridization signal intensity and depends on the type of pre-treatment solution that is selected. Preferably, the effective period of time for pre-treatment of the probes with solutions comprising organic or inorganic compounds is in the range of about 1 minute to about 60 minutes. More preferably, the effective period of time for pre-treatment of the probes with organic solutions or inorganic solutions is about five (5) minutes. Preferably, the effective temperature for pre-treatment of the probes with solutions comprising organic or inorganic compounds is at a temperature in the range of about 20 degrees C. to about 30 degrees C.

Preferably, the effective period of time for pre-treatment of the probes with hot (boiling) water is in the range of about 30 seconds to about 45 minutes. Preferably, with the use of hot (boiling) water as the pre-treatment solution, the probes are pre-treated with the hot (boiling) water having a temperature in the range of about 90 degrees C. to about 97 degrees C.

In pre-treating the probes with the pre-treatment solution, a desired amount of the pre-treatment solution, typically about 100 micoliters ($\mu l$), is applied to a top surface of a clean substrate, such as a standard glass microscope slide. The strips with the attached probe biomolecules may then be deposited onto the pre-treatment solution, such that the side of the strip having the probe biomolecules attached thereto is placed into direct contact with the pre-treatment solution. Preferably, the probe biomolecules are sufficiently soaked with the pre-treatment solution for an effective period of time.

Depending on the pre-treatment solution selected, the probe biomolecules pre-treated with one of the selected pre-treatment solutions and subsequently hybridized with complementary target biomolecules demonstrate an increase in hybridization signal intensity of at least two (2) times higher, as compared to an identical detection method that does not include the pre-treating step. In various embodiments, the improved method has also demonstrated increased hybridization signal intensities in the range of about two (2) times to about twelve (12) times higher, as compared to identical detection methods that do not include the pre-treating step.

The next step of this aspect of the method of the present invention is applying a buffer solution to the pre-treated probe biomolecules. After the probe biomolecules are sufficiently soaked with a selected pre-treatment solution for an effective period of time, the pre-treated probe biomolecules are sufficiently rinsed with a buffer solution for an effective period of time to remove any excess or residual pre-treatment solution. In certain cases, excess pre-treatment solution may adversely affect subsequent steps of the method of the present invention. Preferably, the buffer solution comprises sodium saline citrate; sodium saline phosphate; tetramethylammonium chloride; sodium saline citrate in ethylenediaminetetra-acetic; sodium saline citrate in sodium dodecyl sulfate; sodium saline phosphate in ethylenediaminetetra-acetic; sodium saline phosphate in sodium dodecyl sulfate; tetramethylammonium chloride in ethylenediaminetetra-acetic; tetramethylammonium chloride in sodium dodecyl sulfate; or combinations thereof. However, other suitable buffer solutions may also be used.

An effective amount of the selected buffer solution may preferably be applied to the probe biomolecules in three separate, but subsequent applications, where each fresh application of buffer solution is applied to the probe biomolecules for a period of time of about five (5) minutes. Thus, the buffer solution is preferably applied to the pre-treated probe biomolecules for a minimum total time period of about fifteen (15) minutes. The pH of the buffer solution is preferably in the range of about 7.0 to about 8.0. Once the pre-treated probe biomolecules are sufficiently washed or rinsed with the buffer solution, the pre-treated probe biomolecules are removed from the buffer solution. The next step of this aspect of the method of the present invention is the hybridization step. The pre-treated and buffer-washed probe biomolecules are hybridized with a plurality of complementary target biomolecules to produce or form a hybridized complex product or duplex product. Preferably, the reverse Southern blotting hybridization technique is used with the present invention.

For purposes of this application, the term "target biomolecule" means biological or chemical components in solution that may become bound specifically to complementary bases on the probe biomolecule on the surface of a solid support substrate through the mechanisms of hybridization. The preferred target biomolecules comprise oligonucleotides and polymerase chain reaction (PCR) fragments. However, other suitable target biomolecules may also be used. For purposes of the present invention, the term "polymerase chain reaction fragments" means an amplified nucleic acid sequence. Preferably, the target oligonucleotides comprise natural or synthetic oligonucleotides, such as deoxyribonucleic acid (DNA), ribonucleic acid (RNA), and peptide-nucleic acid (PNA). More preferably, the target oligonucleotide is DNA.

If the selected target biomolecules are double stranded target biomolecules such as polymerase chain reaction (PCR) fragments-double stranded, the target biomolecules must initially be heated or incubated in a container, such as a standard eppendorf tube, to undergo heat denaturation. Double stranded target biomolecules are not capable of undergoing hybridization with single stranded probe biomolecules. However, heating the double stranded target biomolecules causes the double stranded target biomolecules to separate into single stranded target biomolecules, thereby enabling the target biomolecules to undergo hybridization with the probe biomolecules. Preferably, the double stranded target biomolecules are heated to a temperature of about 90 degrees C. to about 97 degrees C. for a time period of about three (3) minutes to about ten (10) minutes. After the double stranded target biomolecules are sufficiently heated at an effective temperature so that they are separated into single stranded biomolecules, the target biomolecules are immediately cooled by preferably placing the container with the target biomolecules onto an ice bath having a temperature of less than about four (4) degrees C., and placing the container on the ice bath for a period of time of about three (3) minutes to about ten (10) minutes. The single stranded fragments must be immediately cooled in order to temporarily freeze them in their native state and set them in place. If such strands are cooled slowly, they may have a tendency to revert back to a double stranded state.

In further preparing the target biomolecules for hybridization, the target biomolecules are prepared in solution. In the present method, about 100 microliters ($\mu l$) of a target solution is prepared by mixing together about 10 microliters of target biomolecule sample and about 90 microliters of a buffer solution. Preferably, the buffer solution comprises sodium saline citrate; sodium saline phosphate; tetramethylammonium chloride; sodium saline citrate in ethylenediaminetetra-acetic; sodium saline citrate in sodium dodecyl sulfate; sodium saline phosphate in ethylenediaminetetra-acetic; sodium saline phosphate in sodium dodecyl sulfate; tetramethylammonium chloride in ethylenediaminetetra-acetic; tetramethylammonium chloride in sodium dodecyl sulfate; or combinations thereof. However, other suitable buffer solutions may also be used. An amount of the prepared target biomolecule solution, typically about 100 $\mu l$, may then be applied to a top surface of a clean substrate, such as a standard glass microscope slide. The standard glass microscope slide may be situated within a container, such as a standard petri dish. The strips of pre-treated, buffer-washed probe biomolecules may then be deposited onto the target biomolecule solution, such that the side of the strip having the probe biomolecules attached thereto is placed into direct contact with the target solution. For purposes of this invention, the length of time over which the probe biomolecules are hybridized with the target biomolecules is an effective period of time which results in complete or substantially complete hybridization. While the probe biomolecules are being treated with the solution containing the target biomolecules, the container in which the probe biomolecules are situated may be shaken in a water bath having a constant temperature in the range of about 20 degrees C. to about 30 degrees C. for an effective period of time in the range of about fifteen (15) minutes to about ninety (90) minutes. The water bath that may be used is the Gemini Twin Shaking Water Bath (manufactured by Robbins Scientific Corporation of Sunnyvale, Calif.). Preferably, the temperature at which the probe biomolecules undergo hybridization with the target biomolecules is at a temperature in the range of about 20 degrees C. to about 30 degrees C.

Once the probe biomolecules and the target biomolecules are sufficiently hybridized to form a hybridized duplex product or complex product, the next step of this aspect of the method of the present invention is to develop and detect a signal of interest, wherein the signal has an increased intensity.

The developing and detecting step may include the use of a detection label. The detection label used to detect the signal of interest may be a radiolabel or a non-radiolabel. The selected label may be applied directly to the target biomolecules to aid in detection of the signal of interest. Preferably, the radiolabel comprises phosphorus-32 ($^{32}P$), sulfur-35 ($^{35}S$), or radioilluminescent compounds. However, other suitable radiolabels may also be used. Preferably, the non-radiolabel comprises enzymes, chemilluminescent compounds, fluorescent compounds, metal complexes, haptenes, phosphatase, colorimetric agents, horseradish peroxidase, or dyes. Other suitable non-radiolabels may be used as well. The preferred non-radiolabel is a non-radio biotinylated-phosphoramidite label (manufactured by Clonetech of Palo Alto, Calif.).

The developing step may further include applying a buffer solution to the hybridized complex. The hybridized complex may be rinsed or washed with a fresh amount of buffer solution. Preferably, the buffer solution comprises sodium saline citrate; sodium saline phosphate; tetramethylammonium chloride; sodium saline citrate in ethylenediaminetetra-acetic; sodium saline citrate in sodium dodecyl sulfate; sodium saline phosphate in ethylenediaminetetra-acetic; sodium saline phosphate in sodium dodecyl sulfate; tetramethylammonium chloride in ethylenediaminetetra-acetic; tetramethylammonium chloride in sodium dodecyl sulfate; or combinations thereof. However, other suitable buffer solutions may also be used. The buffer solution is applied to the hybridized complex in preferably three separate, but subsequent applications, where each fresh application of buffer solution is applied for a period of time of about five (5) minutes. Thus, the buffer solution is preferably applied to the hybridized complex for a minimum of about 15 minutes. Once the hybridized complex is sufficiently washed or rinsed with the buffer solution, the hybridized complex is removed from the buffer solution.

The developing and detecting step may further include the steps of treating the hybridized complex with a conjugating solution, and treating the conjugated, hybridized complex with a detection reagent. However, these steps do not need to be carried out when radiolabels are used with the target biomolecules.

The hybridized complex may be treated after hybridization with a conjugating solution to effect conjugation or coupling of the hybridized complex with the solid support substrate. Preferably, the conjugating solution comprises streptavidin alkaline phosphatase, avidin alkaline phosphatase, or horseradish peroxidase. However, other suitable conjugating solutions may also be used. An amount of 10 μl of conjugating solution may be mixed with 990 μl of buffer solution, such as sodium saline citrate or another suitable buffer as discussed in the buffer step above, for a total of 1000 μl of solution. The hybridized complex is preferably treated with 100 μl of the diluted conjugating solution. Preferably, the hybridized complex is treated with the conjugating solution at a temperature in the range of about 20 degrees C. to about 30 degrees C. and for a time period of in the range of about thirty (30) minutes to about ninety (90) minutes. The conjugated, treated, hybridized complex may then be rinsed with a fresh amount of buffer solution, such as sodium saline citrate or another suitable buffer solution, as discussed in the buffer step above, and for a time period of about five (5) minutes, with shaking. The buffer rinsing step may be repeated for two additional five (5) minute periods.

The conjugated, hybridized complex may then be treated with a selected detection reagent. Preferably, the detection reagent comprises enzyme-labeled fluorescence reagents or calorimetric reagents. More preferably, the detection reagent is enzyme-labeled fluorescence reagent ELF) from Molecular Probes, Inc. of Eugene, Oreg. The hybridized complex is treated with about 100 μl of the detection reagent for about thirty (30) minutes to about ninety (90) minutes at a temperature in the range of about 20 degrees C. to about 30 degrees C. The strip carrying the hybridized complex is then carefully dipped a single time into a buffer solution, such as sodium saline citrate or another suitable buffer, as discussed in the buffer step above, to remove excess detection reagent.

The hybridized complex may then be placed on a detection device, such as an ultraviolet (UV) transilluminator (manufactured by UVP, Inc. of Upland, Calif.). The signal is developed and the increased signal intensity may be recorded with a recording device, such as a charge coupled device (CCD) camera (manufactured by Photometrics, Inc. of Tucson, Ariz.). Several different models of CCD cameras were used with the method of the present invention. For fluorescent label detection, a cooled CCD camera system (Photometrics Model CH250) may be mounted to a copy stand and the camera lens may be positioned directly above the polypropylene film. For the signals developed with radiolabels, the signal intensity data was collected with a PhosphorImager, SF automatic scanner device manufactured by Molecular Dynamics, Inc. of Sunnyvale, Calif.).

Another source of light or illumination unit that may be used with the present invention is an OMNIPRINT 1000 forensics illumination unit from Omnichrome of Chino, Calif. This unit is used to excite fluorescence from the non-radiolabeled targets bound to the polypropylene films. Images may be analyzed and plotted using National Institute of Health (NIH) Image software.

The present invention also provides for a kit for detecting hybridized biomolecules. The kit comprises a plurality of probe biomolecules on a solid polypropylene support surface; an effective amount of a pre-treatment solution for application to the probe biomolecules to produce a signal of interest having an increased intensity of at least two (2) times, as compared to probe biomolecules that are not pre-treated with the pre-treatment solution; a buffer solution; a plurality of target biomolecules for hybridization with the probe biomolecules to form a hybridized complex; a conjugating solution for developing the signal of interest; and, a detection reagent for detecting the signal of interest. The probe biomolecules may comprise oligonucleotides such as deoxyribonucleic acid, ribonucleic acid, and peptide-nucleic acid. The buffer solution may comprise a buffer such as one of the buffers discussed in the buffer step above. The pre-treatment solution may comprise one of the pre-treatment solutions as discussed in the pre-treatment step above. The target biomolecules may comprise oligonucleotides such as deoxyribonucleic acid, ribonucleic acid, and peptide-nucleic acid, or may comprise polymerase chain reaction fragments. The target biomolecules may be in the form of and used as a standard control. The conjugating solution for developing the signal of interest may comprise one of the conjugating solutions discussed above in the step of treating the hybridized complex with a conjugating solution. The detection reagent for detecting the signal of interest may be selected from one of the detection reagents discussed above in the step of treating the hybridized complex with a detection reagent.

FIG. 3 illustrates a typical array panel spread sheet (internally labeled 17F) used in the method of the present invention and used to obtain the signal information in the Examples set forth below. In FIG. 3, the bands (probe sequences) labeled 1, 2, 41, and 64 represent poly-A marker bands that are used to check the quality control of the synthesis. Bands 3–40 represent the wild type probe sequences. Bands 42–63 represent the mutant probe sequences with a point mutation from base G to base T in codon 12/13, where the base T mutation is shown in boldface. With the mutant probe sequences, it is found that hybridization with PCR targets is more favorable than hybridization with synthetic targets.

The spreadsheet in FIG. 3 is for an H-ras oncogene (cancer gene) Exon 1 codon 12/13 (sense) in which the probes are attached to the substrate in the direction from the 3' (prime) position to the 5' (prime) position, with the 3' position attached to the substrate surface. H-ras is a naturally occurring gene which occasionally converts to an activated form. The probes are sense strands. The targets are antisense strands. The spreadsheet is designed to have a maximum of 64 bands. Some of the probe sequences are duplicated on the spreadsheet (i.e., bands 3 and 4; bands 5 and 6) so that tests may be duplicated if desired.

An array of probe biomolecules consisting of oligonucleotides complementary either to wild type or to one particular mutant sequence of the H-ras oncogene is used in the Examples set forth below. Elements in the array varied in length from ten (10) to eighteen (18) bases, varied in placement within their full length from ten (10) to eighteen (18) bases, and varied in placement within their full length target sequences.

The target sequences used in the Examples set forth below include the following:
(1) Target: A-918 synthetic target/H-ras Wild Type Antisense Strand (Biotin labeled-10 mer)
   5'-Biotin-ACA-CCG-CCG-G-3'
(2) Target: A-902 synthetic target/H-ras Wild Type Antisense Strand (Radiolabeled-10 mer)
   5'-$^{32}$P-ACA-CCG-CCG-G-3'
(3) Target: 63 base pair PCR H-ras Wild Type Antisense Strand (Biotin labeled)
   (Codons 12 & 13 are at positions 1697–1702 in the gene).
   5'Biotin TG GAT GGT CAG CGC ACT CTT GCC CAC ACC GCC GGC GCC CAC CAC CAC CAG CTT ATA TTC CGT C3'
(4) Target: 109 Base Pair PCR H-ras Wild Type Antisense Strand (Radiolabeled)
   (Codons 12 & 13 are at positions 1697–1702 in the gene).
   5'-$^{32}$P CTC TAT AGT GGG GTC GTA TTC GTC CAC AAA ATG GTT CTG GAT CAG CTG GAT GGT CAG CGC ACT CTT GCC CAC ACC GCC GGC GCC CAC CAC CAC CAG CTT ATA TTC CGT C3'

In most of the Examples discussed below, hybridization buffers of sodium saline citrate having a concentration strength of about 2X to 6X, and sodium saline phosphate having a concentration strength of about 2X to 6X, were prepared from dilutions of sodium saline citrate having a concentration strength of about 20X, and sodium saline phosphate having a concentration strength of about 20X, respectively. In many cases, the addition of 0.01% sodium dodecyl sulfate (volume per volume) was also made to the buffer solution. The pH of the buffer solution used in the Examples below is in the range of about 7.0 to about 8.0.

In most of the Examples, the hybridized complex is conjugated with avidin-alkaline phosphatase. A fluorescent signal is developed by treatment with an enzyme labeled fluorescence (ELF) reagent from Molecular Probes, Inc. When probe oligonucleotides are pre-treated with the pre-treatment solutions of the present invention and then hybridized with complementary target oligonucleotides, increased hybridization signal intensity is demonstrated. It is also observed that the pre-treated probes produced sharper and more uniform signals than the non-pre-treated control probes. As shown in FIGS. 4–14, the light band portions of each strip in the FIGS. represent areas of weak or little hybridization, and the dark band portions of each strip represent areas of strong or considerable hybridization.

The increased signal intensity is calculated in arbitrary units comprising analog to digital converted (ADC) numbers. The increased signal intensity is indicated in the Tables set forth below by the ratio of the average mean signal intensity (visible bands) of the pre-treated probes to the non-pre-treated control. The ratio of the average mean signal intensity of the visible bands is calculated by taking the average mean signal intensity of the visible bands of the pre-treated probes, and dividing that number by the average mean signal intensity of the visible bands of the control probe or strip. Variations in increased signal intensities may depend on base composition, the existence of any secondary structures, and the length of the sequences.

EXAMPLE 1

Oligonucleotide probes were pre-treated with the following various concentrations of sodium hydroxide (NaOH) in 10 millimolar ethylenediaminetetra-acetic acid (EDTA), in 0.01% sodium dodecyl sulfate (SDS): 0.2 M NaOH; 0.4 M NaOH; 0.6M NaOH; 1.0 M NaOH; 1.5 M NaOH; and 2.0 M NaOH. The probes were each separately pre-treated with one of the selected concentrations of NaOH for a time period of about 5 minutes at a temperature of about 22 degrees C. The pre-treated probes were rinsed with a buffer as prepared and discussed above to remove excess pre-treatment solution. The pre-treated probes were exposed to synthetic A-918 targets, under hybridizing conditions. The hybridized complex was conjugated with avidin-alkaline phosphatase. A fluorescent signal was developed by treatment with an enzyme labeled fluorescence (ELF) reagent.

Figure 4:
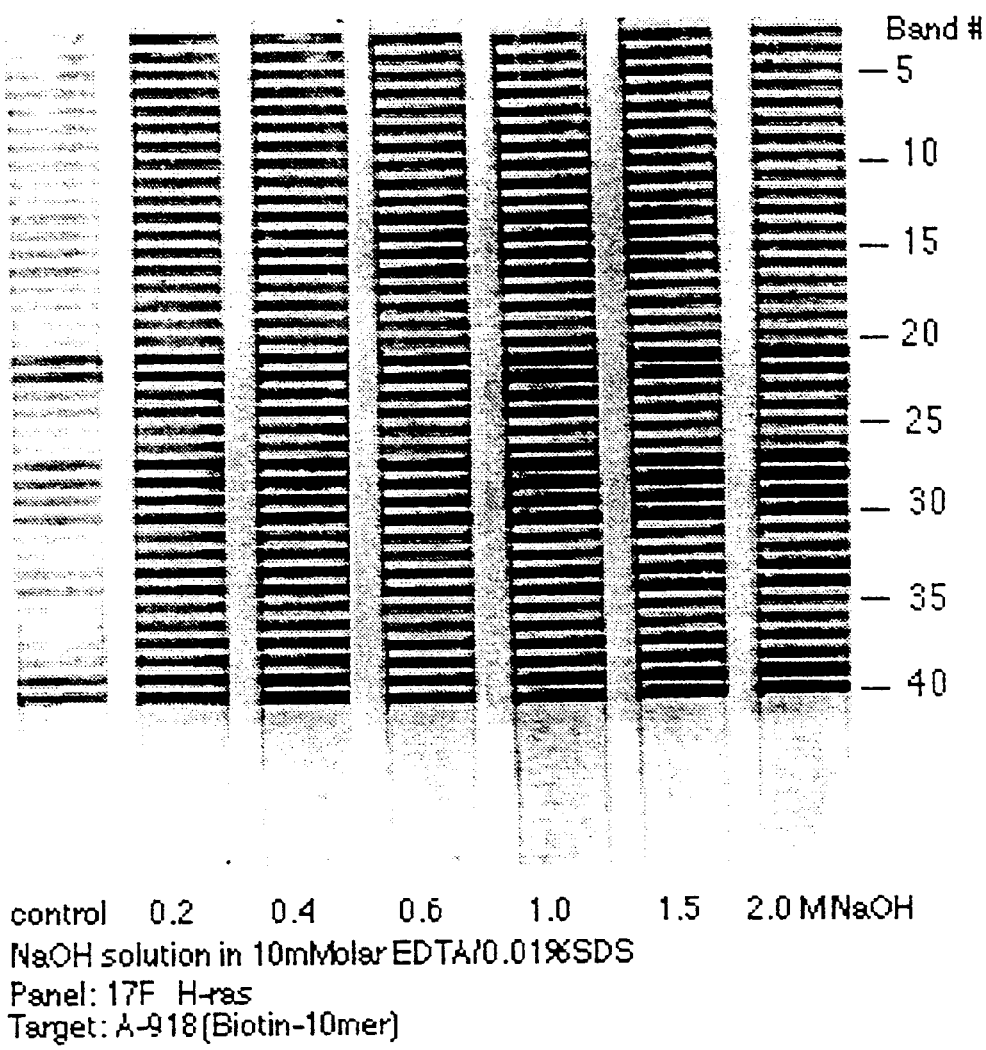
FIG. 4 is a laser printed reproduction of the signal intensities of oligonucleotide probes pre-treated with various concentrations of sodium hydroxide (NaOH) in 10 millimolar ethylenediaminetetra-acetic acid (EDTA) in 0.01% sodium dodecyl sulfate (SDS), and hybridized with synthetic A-918 (biotin-10 mer) oligonucleotide targets, and compared to a standard control, non-pre-treated strip, with detection via a charge coupled device (CCD) camera.

FIG. 4 is a laser printed reproduction of the signal intensities of oligonucleotide probes pre-treated with various concentrations of sodium hydroxide (NaOH) in 10 millimolar ethylenediaminetetra-acetic acid (EDTA), in 0.01% sodium dodecyl sulfate (SDS), and hybridized with synthetic A-918 (biotin-10 mer) oligonucleotide targets, as compared to a standard control, non-pre-treated strip. Detection was made via a CCD camera.

The increased hybridization signal intensities for the various NaOH pre-treated probes, as compared to the signal intensity of the standard control, non-pre-treated probe are set forth in Table 1 below.

TABLE 1

| Control/Pre-Treatment Solution NaOH M (Molar) | Average Mean Signal Intensity (Visible Bands) | Ratio of Average Mean Signal Intensity (Visible Bands) of the Pre-Treated Probes to the Control |
| --- | --- | --- |
| Control | 221 | — |
| 0.2M NaOH | 857 | 3.88 |
| 0.4M NaOH | 1295 | 5.86 |
| 0.6M NaOH | 1319 | 5.97 |
| 1.0M NaOH | 1964 | 8.89 |
| 1.5M NaOH | 1864 | 8.43 |
| 2.0M NaOH | 1424 | 6.44 |

EXAMPLE 2

Oligonucleotide probes were pre-treated with the following various concentrations of sodium hydroxide (NaOH) in 10 millimolar ethylenediaminetetra-acetic acid (EDTA), in 0.01% sodium dodecyl sulfate (SDS): 0.4 M NaOH; 0.6 M NaOH; 0.8 M NaOH; and 1.0 M NaOH. The probes were each separately pre-treated with one of the selected concentrations of NaOH for a time period of about 5 minutes at a temperature of about 22 degrees C. The pre-treated probes were rinsed with a buffer to remove excess pre-treatment solution. The pre-treated probes were exposed to 63 base pair wild type polymerase chain reaction (PCR) targets, under hybridizing conditions. The hybridized complex was conjugated with avidin-alkaline phosphatase. A fluorescent signal was developed by treatment with an enzyme labeled fluorescence (ELF) reagent.

Figure 5:
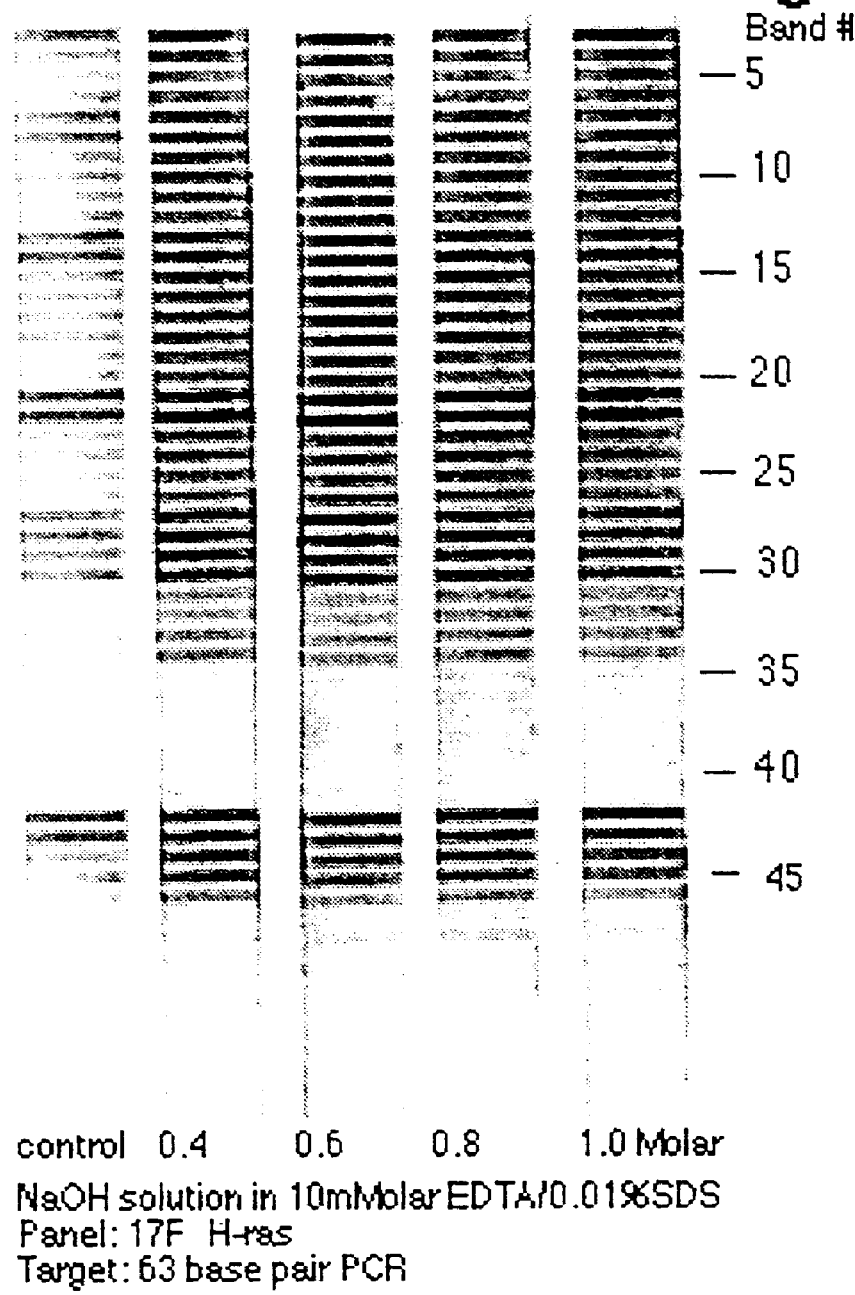
FIG. 5 is a laser printed reproduction of the signal intensities of oligonucleotide probes pre-treated with various concentrations of sodium hydroxide (NaOH) in 10 millimolar ethylenediaminetetra-acetic acid (EDTA) in 0.01% sodium dodecyl sulfate (SDS), and hybridized with 63 base pair wild type polymerase chain reaction (PCR) targets, and compared to a standard control, non-pre-treated strip, with detection via a charge coupled device (CCD) camera.

FIG. 5 is a laser printed reproduction of the signal intensities of the oligonucleotide probes pre-treated with the various concentrations of sodium hydroxide (NaOH) in 10 millimolar ethylenediaminetetra-acetic acid (EDTA), in 0.01% sodium dodecyl sulfate (SDS), and hybridized with 63 base pair wild type polymerase chain reaction (PCR) targets, as compared to a standard control, non-pre-treated strip. Detection was made via a CCD camera.

The increased hybridization signal intensities for the various NaOH pre-treated probes, as compared to the signal intensity of the standard control, non-pre-treated probe are set forth in Table 2 below.

TABLE 2

| Control/Pre-Treatment Solution NaOH M (Molar) | Average Mean Signal Intensity (Visible Bands) | Ratio of Average Mean Signal Intensity (Visible Bands) of the Pre-Treated Probes to the Control |
| --- | --- | --- |
| Control | 630 | — |
| 0.4M NaOH | 1626 | 2.62 |
| 0.6M NaOH | 1649 | 2.65 |
| 0.8M NaOH | 1836 | 2.96 |
| 1.0M NaOH | 1875 | 3.02 |

EXAMPLE 3

Oligonucleotide probes were pre-treated with 1.0 M sodium hydroxide (NaOH) in 10 millimolar ethylenediaminetetra-acetic acid (EDTA), in 0.01% sodium dodecyl sulfate (SDS), for the following various periods of time: 5 minutes; 10 minutes; 20 minutes; 40 minutes; and 60 minutes. The probes were each separately pre-treated with the NaOH solution at a temperature of about 22 degrees C. The pre-treated probes were rinsed with a buffer to remove excess pre-treatment solution. The pre-treated probes were exposed to synthetic A-918 (biotin-10 mer) oligonucleotide targets, under hybridizing conditions. The hybridized complex was conjugated with avidin-alkaline phosphatase. A fluorescent signal was developed by treatment with an enzyme labeled fluorescence (ELF) reagent.

Figure 6:
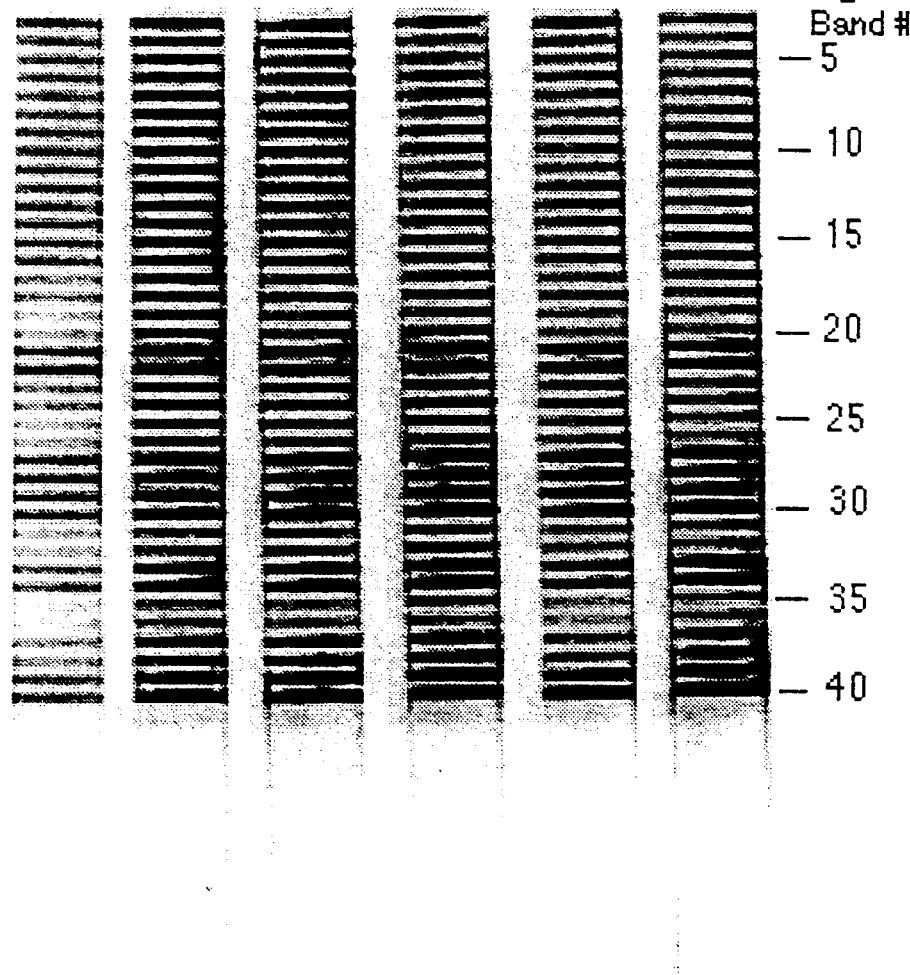
FIG. 6 is a laser printed reproduction of the signal intensities of oligonucleotide probes pre-treated with 1.0 M sodium hydroxide (NaOH) solution in 10 millimolar ethylenediaminetetra-acetic acid (EDTA) in 0.01% sodium dodecyl sulfate (SDS), for various periods of time, and hybridized with synthetic A-918 (biotin-10 mer) oligonucleotide targets, and compared to a standard control, non-pre-treated strip, with detection via a charge coupled device (CCD) camera.

FIG. 6 is a laser printed reproduction of the signal intensities of the oligonucleotide probes pre-treated with 1.0 M sodium hydroxide (NaOH) in 10 millimolar ethylenediaminetetra-acetic acid (EDTA), in 0.01% sodium dodecyl sulfate (SDS), for various periods of time, and hybridized with synthetic A-918 targets, as compared to a standard control, non-pre-treated strip. Detection was made via a CCD camera.

The increased hybridization signal intensities for the NaOH pre-treated probes over varying time periods, as compared to the signal intensity of the standard control, non-pre-treated probe are set forth in Table 3 below.

TABLE 3

| Control/Probes Pre-Treated with 1.0M NaOH Solution/Time(Minutes) | Average Mean Signal Intensity Visible Bands | Ratio of Average Mean Signal Intensity (Visible Bands) of the Pre-Treated Probes to the Control |
| --- | --- | --- |
| Control | 334 | — |
| 5 minutes | 1419 | 4.24 |
| 10 minutes | 1416 | 4.23 |
| 20 minutes | 1294 | 3.87 |
| 40 minutes | 1003 | 3.00 |
| 60 minutes | 1075 | 3.21 |

EXAMPLE 4

Oligonucleotide probes were pre-treated with 1.0 M sodium hydroxide (NaOH) in 10 millimolar ethylenediaminetetra-acetic acid (EDTA), in 0.01% sodium dodecyl sulfate (SDS), for the following various periods of time: 5 minutes; 20 minutes; 40 minutes; and 60 minutes. The probes were each separately pre-treated with the NaOH solution at a temperature of about 22 degrees C. The pre-treated probes were rinsed with a buffer to remove excess pre-treatment solution. The pre-treated probes were exposed to 63 base pair wild type polymerase chain reaction (PCR) targets, under hybridizing conditions. The hybridized complex was conjugated with avidin-alkaline phosphatase. A fluorescent signal was developed by treatment with an enzyme labeled fluorescence (ELF) reagent.

Figure 7:
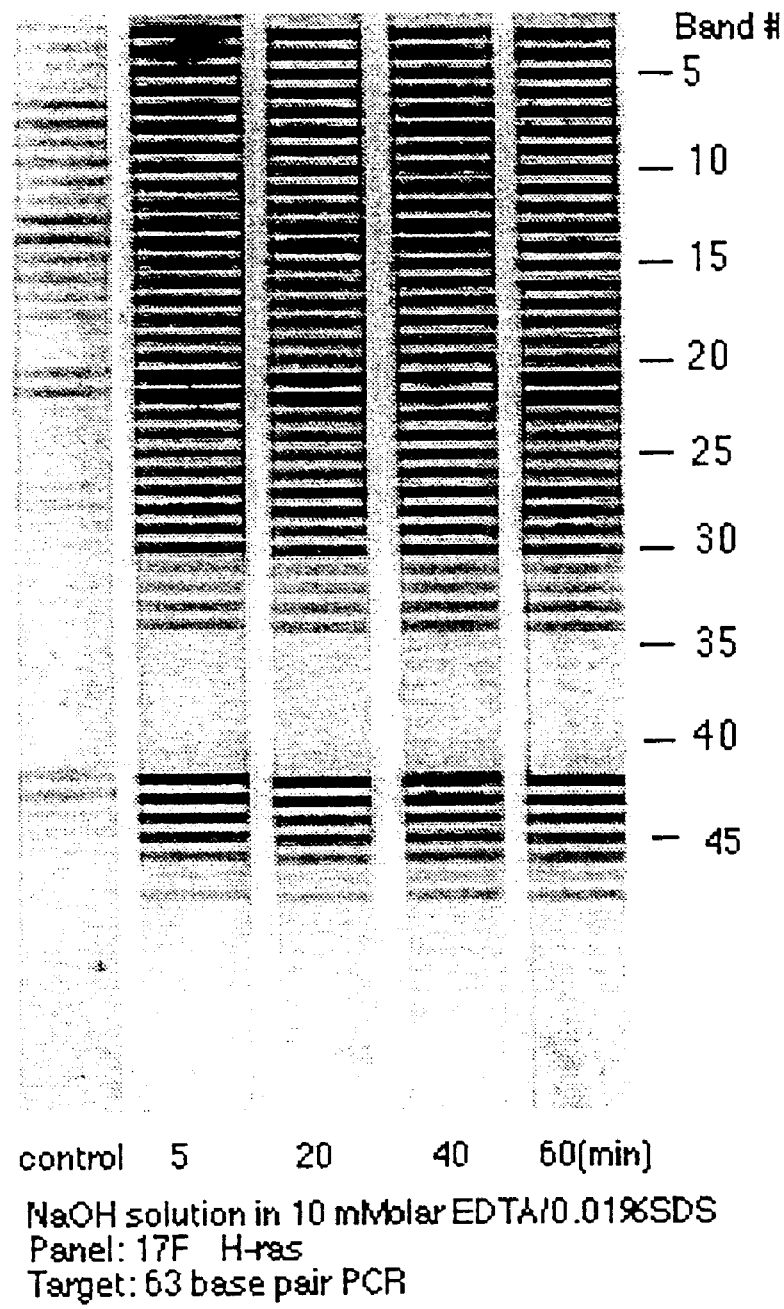
FIG. 7 is a laser printed reproduction of the signal intensities of oligonucleotide probes pre-treated with 1.0 M sodium hydroxide (NaOH) solution in 10 millimolar ethylenediaminetetra-acetic acid (EDTA) in 0.01% sodium dodecyl sulfate (SDS), for various periods of time, and hybridized with 63 base pair wild type polymerase chain reaction (PCR) targets, and compared to a standard control, non-pre-treated strip, with detection via a CCD camera.

FIG. 7 is a laser printed reproduction of the signal intensities of the oligonucleotide probes pre-treated with 1.0 M sodium hydroxide (NaOH) in 10 millimolar ethylenediaminetetra-acetic acid (EDTA), in 0.01% sodium dodecyl sulfate (SDS), for various periods of time, and hybridized with 63 base pair wild type polymerase chain reaction (PCR) targets, as compared to a standard control, non-pre-treated strip. Detection was made via a CCD camera.

The increased hybridization signal intensities for the NaOH pre-treated probes over varying time periods, as compared to the signal intensity of the standard control, non-pre-treated probe are set forth in Table 4 below.

TABLE 4

| Control/ Probes Pre-Treated with 1.0M NaOH Solution/ Time(Minutes) | Average Mean Signal Intensity Visible Bands | Ratio of Average Mean Signal Intensity (Visible Bands) of the Pre-Treated Probes to the Control |
|---|---|---|
| Control | 169 | — |
| 5 minutes | 2005 | 11.83 |
| 20 minutes | 1467 | 8.65 |
| 40 minutes | 1744 | 10.29 |
| 60 minutes | 1741 | 10.27 |

EXAMPLE 5

Example 5 shows the results of an experiment conducted for reproducibility purposes. Oligonucleotide probes were all pre-treated with 1.0 M sodium hydroxide (NaOH) in 10 millimolar ethylenediaminetetra-acetic acid (EDTA), in 0.01% sodium dodecyl sulfate (SDS). The probes were each separately pre-treated with 1.0 M NaOH solution for a time period of about 5 minutes and at a temperature of about 22 degrees C. The pre-treated probes were rinsed with a buffer to remove excess pre-treatment solution. The pre-treated probes were exposed to 63 base pair wild type polymerase chain reaction (PCR) targets, under hybridizing conditions. The hybridized complex was conjugated with avidin-alkaline phosphatase. A fluorescent signal was developed by treatment with an enzyme labeled fluorescence (ELF) reagent.

Figure 8:
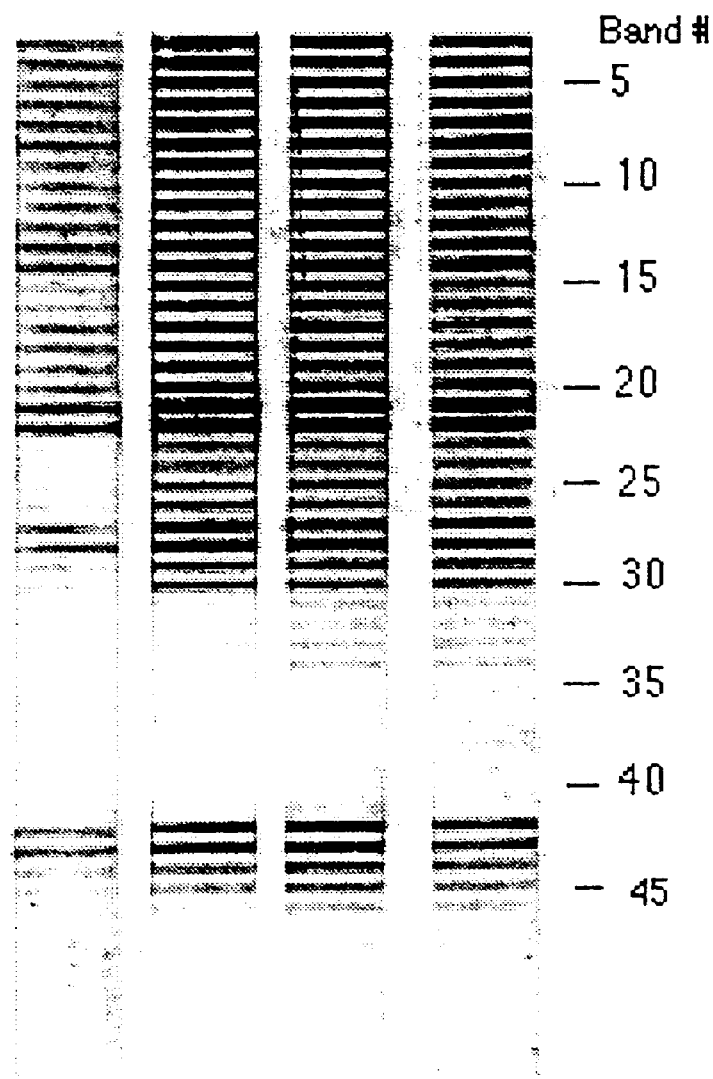
FIG. 8 is a laser printed reproduction showing reproducibility of the signal intensities of oligonucleotide probes pre-treated with 1.0 M sodium hydroxide (NaOH) in 10 millimolar ethylenediaminetetra-acetic acid (EDTA) in 0.01% sodium dodecyl sulfate (SDS), and hybridized with 63 base pair wild type polymerase chain reaction (PCR) targets, and compared to a standard control, non-pre-treated strip, with detection via a CCD camera.

FIG. 8 is a laser printed reproduction showing reproducibility of the signal intensities of the oligonucleotide probes pre-treated with 1.0 M NaOH in 10 millimolar EDTA in 0.01% sodium dodecyl sulfate, and hybridized with the PCR targets, as compared to a standard control, non-pre-treated strip. Detection was made via a CCD camera.

The increased hybridization signal intensities for the NaOH pre-treated probes, as compared to the signal intensity of the standard control, non-pre-treated probe are set forth in Table 5 below.

TABLE 5

| Control/ Pre-Treatment Solution 1.0M (Molar) NaOH | Average Mean Signal Intensity (Visible Bands) | Ratio of Average Mean Signal Intensity (Visible Bands) of the Pre-Treated Probes to the Control |
|---|---|---|
| Control | 339 | — |
| 1.0M NaOH | 1238 | 3.65 |
| 1.0M NaOH | 1110 | 3.27 |
| 1.0M NaOH | 1030 | 3.04 |

EXAMPLE 6

Oligonucleotide probes were pre-treated with various alkali salt solutions in 10 millimolar ethylenediaminetetra-acetic acid (EDTA), in 0.01% sodium dodecyl sulfate (SDS), including the following: 1.0 M sodium hydroxide (NaOH); 1.5 M sodium hydroxide (NaOH); 1.5 M sodium chloride (NaCl); 1.5 M potassium chloride (KCl); 1.5 M lithium chloride (LiCl); 1.5 M sodium bicarbonate ($Na_2CO_3$); and, (7) 1.5 M sodium acetate (NaOAc). The probes were each separately pre-treated with the various alkali salt solutions for a time period of about 5 minutes and at a temperature of about 22 degrees C. The pre-treated probes were rinsed with a buffer to remove excess pre-treatment solution. The pre-treated probes were exposed to 63 base pair wild type polymerase chain reaction (PCR) targets, under hybridizing conditions. The hybridized complex was conjugated with avidin-alkaline phosphatase. A fluorescent signal was developed by treatment with an enzyme labeled fluorescence (ELF) reagent.

Figure 9:
FIG. 9 is a laser printed reproduction of the signal intensities of oligonucleotide probes pre-treated with various alkali salt solutions in 10 millimolar ethylenediaminetetra-acetic acid (EDTA) in 0.01% sodium dodecyl sulfate (SDS), and hybridized with 63 base pair wild type polymerase chain reaction (PCR) targets, and compared to a standard control, non-pre-treated strip, with detection via a CCD camera.

FIG. 9 is a laser printed reproduction of the signal intensities of the oligonucleotide probes pre-treated with 1.0 M NaOH; 1.5 M NaOH; 1.5 M NaCl; 1.5 M KCl; 1.5 M LiCl; 1.5 M $Na_2CO_3$; and, 1.5 M NaOAc; and, hybridized with 63 base pair wild type polymerase chain reaction (PCR) targets, as compared to a standard control, non-pre-treated strip. Detection was made via a CCD camera.

The increased hybridization signal intensities for the probes pre-treated with various alkali salts, as compared to the signal intensity of the standard control, non-pre-treated probe are set forth in Table 6 below. The data in Table 6 shows that elements in the pre-treated arrays are in all cases more intensely labeled than the corresponding elements in the non-pre-treated array.

TABLE 6

| Control/ Pre-Treatment Solution Alkali Salt Solutions M (Molar) | Average Mean Signal Intensity (Visible Bands) | Ratio of Average Mean Signal Intensity (Visible Bands) of the Pre-Treated Probes to the Control |
|---|---|---|
| Control | 298 | — |
| 1.0M NaOH | 1946 | 6.53 |
| 1.5M NaOH | 1861 | 6.25 |
| 1.5M NaCl | 1355 | 4.55 |
| 1.5M KCl | 1461 | 4.90 |
| 1.5M LiCl | 893 | 3.00 |
| 1.5M $Na_2CO_3$ | 1357 | 4.55 |
| 1.5M NaOAc | 1012 | 3.40 |

EXAMPLE 7

Oligonucleotide probes were pre-treated with the following various organic reagents: 7.0M urea in 10 millimolar ethylenediaminetetra-acetic acid (EDTA), in 0.01% sodium dodecyl sulfate (SDS); 2.0 M guanidine hydrochloric acid (HCl) in 10 millimolar ethylenediaminetetra-acetic acid (EDTA), in 0.01% sodium dodecyl sulfate (SDS); 99% 1,1,3,3-tetramethyl urea in 0.01% sodium dodecyl sulfate (SDS); and (4) 99% formamide in 0.01% sodium dodecyl sulfate (SDS). The probes were each separately pre-treated with the various organic reagents for a time period of about 5 minutes and at a temperature of about 22 degrees C. The pre-treated probes were rinsed with a buffer to remove excess pre-treatment solution. The pre-treated probes were exposed to 63 base pair wild type polymerase chain reaction (PCR) targets, under hybridizing conditions. The hybridized complex was conjugated with avidin-alkaline phosphatase. A fluorescent signal was developed by treatment with an enzyme labeled fluorescence (ELF) reagent.

Figure 10:
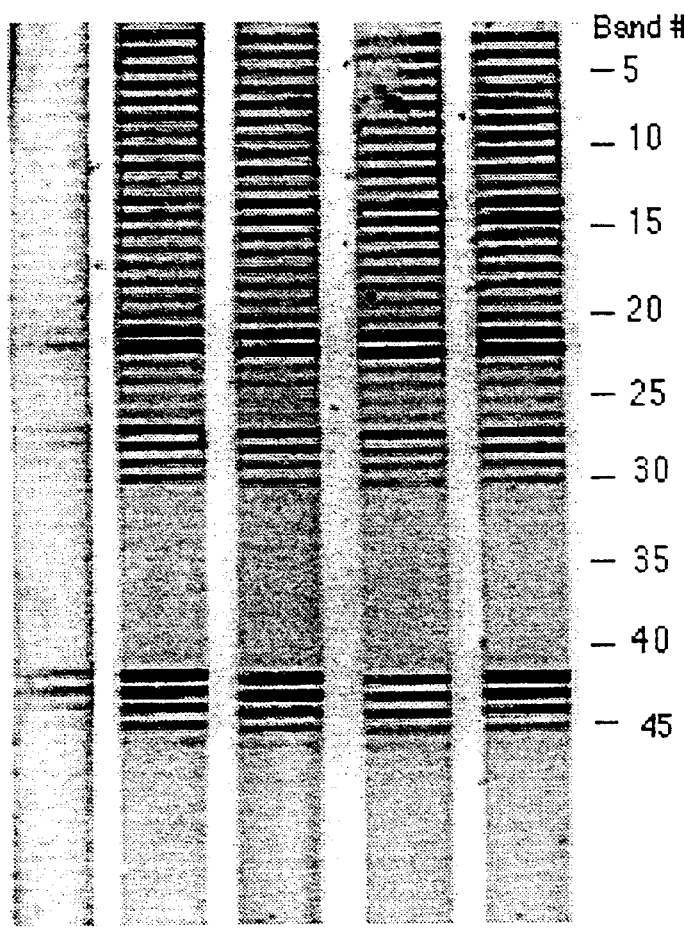
FIG. 10 is a laser printed reproduction of the signal intensities of oligonucleotide probes pre-treated with various organic reagents, and hybridized with 63 base pair wild type polymerase chain reaction (PCR) targets, and compared to a standard control, non-pre-treated strip, with detection via a CCD camera.

FIG. 10 is a laser printed reproduction of the signal intensities of oligonucleotide probe pre-treated with the various following organic reagents: 7.0 M urea in 10 millimolar ethylenediaminetetra-acetic acid (EDTA), in 0.01% sodium dodecyl sulfate (SDS); 2.0 M guanidine HCl in 10 millimolar ethylenediaminetetra-acetic acid (EDTA), in 0.01% sodium dodecyl sulfate (SDS); 99% 1,1,3,3- tetramethyl urea in 0.01% sodium dodecyl sulfate (SDS); and (4) 99% formamide in 0.01% sodium dodecyl sulfate (SDS); and, hybridized with 63 base pair wild type polymerase chain reaction (PCR) targets, as compared to a standard control, non-pre-treated strip. Detection was via a CCD camera.

The increased hybridization signal intensities for the probes pre-treated with the various organic reagents, as compared to the signal intensity of the standard control, non-pre-treated probe are set forth in Table 7 below.

TABLE 7

| Control/ Pre-Treatment Solution Organic Reagents M (Molar) | Average Mean Signal Intensity (Visible Bands) | Ratio of Average Mean Signal Intensity (Visible Bands) of the Pre-Treated Probes to the Control |
| --- | --- | --- |
| Control | 21 | — |
| 7.0M urea in EDTA in SDS | 91 | 4.43 |
| 2.0M guanidine HCl in EDTA in SDS | 92 | 4.46 |
| 99% tetramethyl urea in SDS | 81 | 3.92 |
| 99% formamide in SDS | 103 | 4.97 |

EXAMPLE 8

Oligonucleotide probes were pre-treated with hot (boiling) water at 95 degrees C. for various time periods, including the following: 5 minutes; 10 minutes; and 15 minutes. The probe oligonucleotide strips were exposed to synthetic A-918 (biotin-10 mer) targets, under hybridizing conditions. The hybridized complex was conjugated with avidin-alkaline phosphatase. A fluorescent signal was developed by treatment with enzyme labeled fluorescence (ELF).

Figure 11:
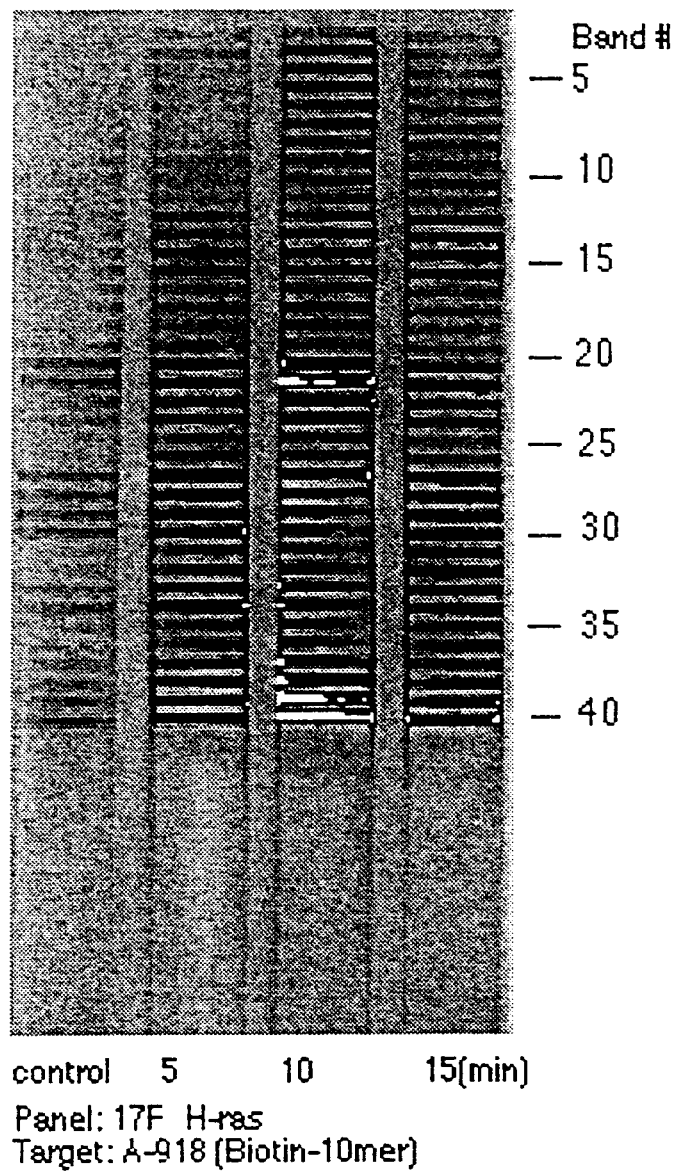
FIG. 11 is a laser printed reproduction of the signal intensities of oligonucleotide probes pre-treated with hot (boiling) water at 95 degrees C. for various periods of time, and hybridized with synthetic A-918 (biotin-10 mer) oligonucleotide targets, and compared to a standard control, non-pre-treated strip, with detection via a charge coupled device (CCD) camera.

FIG. 11 is a laser printed reproduction of the signal intensities of oligonucleotide probes pre-treated with hot (boiling) water at 95 degrees C. for various periods of time, and hybridized with synthetic A-918 (biotin-10 mer) oligonucleotide targets, as compared to a standard control, non-pre-treated strip. Detection was via a CCD camera.

The increased hybridization signal intensities for the probes pre-treated with hot (boiling) water, as compared to the signal intensity of the standard control, non-pre-treated probe are set forth in Table 8 below.

TABLE 8

| Control/ Pre-Treated With Hot (Boiling) Water at 95EC/ Time (Minutes) | Average Mean Signal Intensity (Visible Bands) | Ratio of Average Mean Signal Intensity (Visible Bands) of the Pre-Treated Probes to the Control |
| --- | --- | --- |
| Control | 3.78 | — |
| 5 minutes | 23.26 | 6.16 |
| 10 minutes | 31.58 | 8.36 |
| 15 minutes | 25.13 | 6.65 |

EXAMPLE

Oligonucleotide probes were pre-treated with hot (boiling) water at 95 degrees C. for a time period of 5 minutes. The probes were exposed to 63 base pair polymerase chain reaction (PCR) targets, under hybridizing conditions. The hybridized complex was conjugated with avidin-alkaline phosphatase. A fluorescent signal was then developed by treatment with enzyme labeled fluorescence (ELF).

Figure 12:
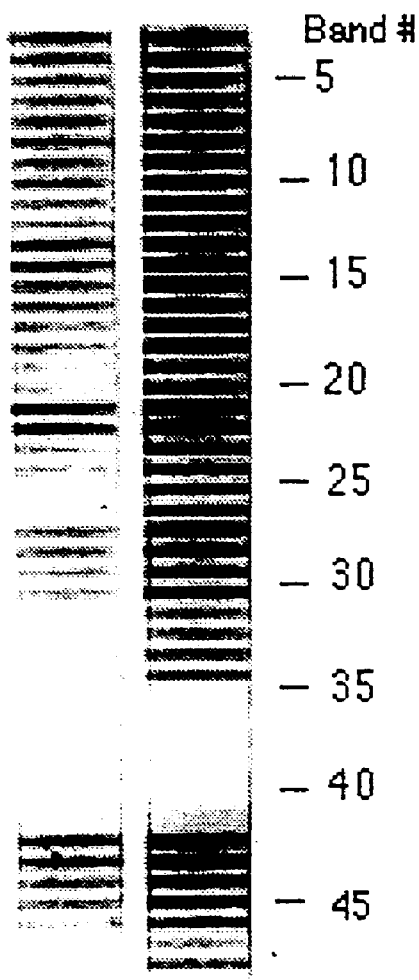
FIG. 12 is a laser printed reproduction of the signal intensities of oligonucleotide probes pre-treated with hot (boiling) water at 95 degrees C. for a five (5) minute period of time, and hybridized with 63 base pair wild type polymerase chain reaction (PCR) targets, and compared to a standard control, non-pre-treated strip, with detection via a charge coupled device (CCD) camera.

FIG. 12 is a laser printed reproduction of the signal intensities of oligonucleotide probes pre-treated with hot (boiling) water at 95 degrees C. for a five (5) minute period of time, and hybridized with 63 base pair wild type polymerase chain reaction (PCR) targets, as compared to astandard control, non-pre-treated strip. Detection was via a charge coupled device (CCD) camera.

The increased hybridization signal intensities for the probes pre-treated with hot (boiling) water, as compared to the signal intensity of the standard control, non-pre-treated probe are set forth in Table 9 below.

TABLE 9

| Control/ Pre-Treated With Hot (Boiling) Water at 95EC/ Time (Minutes) | Average Mean Signal Intensity (Visible Bands) | Ratio of Average Mean Signal Intensity (Visible Bands) of the Pre-Treated Probes to the Control |
| --- | --- | --- |
| Control | 261 | — |
| 5 minutes | 1452 | 5.57 |

EXAMPLE 10

Improvement in signal intensity was also demonstrated when synthetic A-902 target biomolecules were initially labeled with a radiolabel. Oligonucleotide probes were pre-treated with I.0M sodium hydroxide (NaOH), in 10 millimolar ethylenediaminetetra-acetic acid (EDTA), in 0.01% sodium dodecyl sulfate (SDS), for about 5 minutes at about 22 degrees C. The pre-treated probes were rinsed with a fresh amount of sodium saline citrate buffer for three separate 5 minute time periods to remove excess pre-treatment solution. The pre-treated probes were hybridized with complementary $5'^{32}P$ radiolabeled synthetic A-902 targets.

Figure 13:
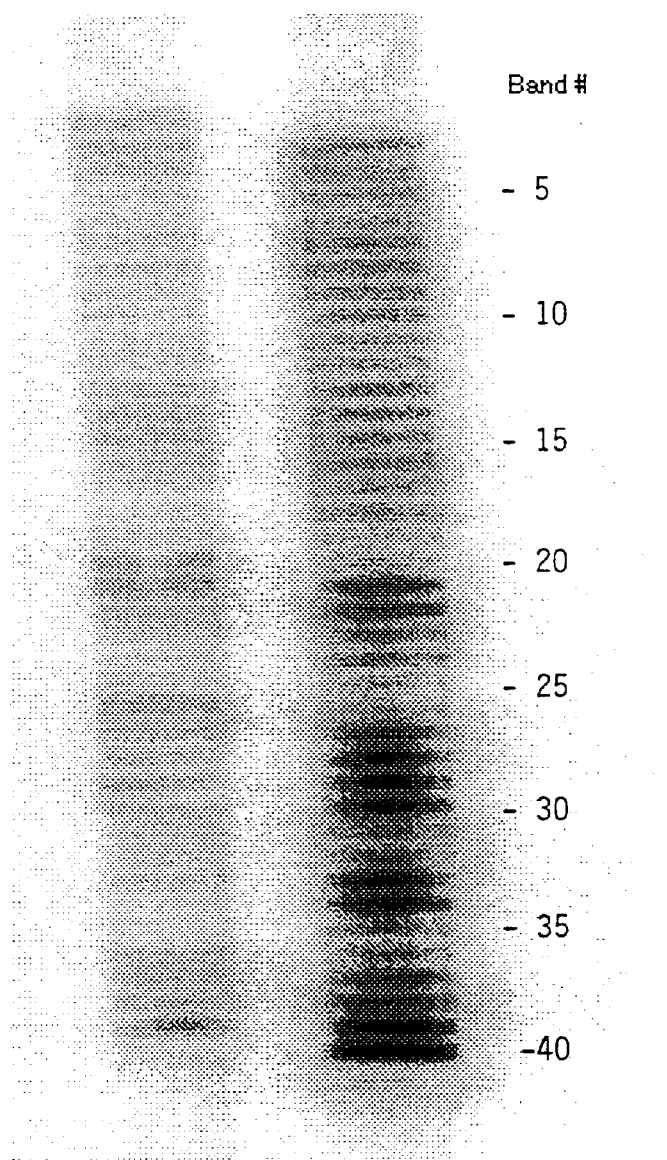
FIG. 13 is a laser printed reproduction of the signal intensities of oligonucleotide probes pre-treated with 1.0 M sodium hydroxide (NaOH) in 10 millimolar ethylenediaminetetra-acetic acid (EDTA) in 0.01% sodium dodecyl sulfate (SDS), and hybridized with $^{32}$P radiolabeled, (10 mer) synthetic A-902 oligonucleotide targets, and compared to a standard control, non-pre-treated strip, with detection via a PhosphorImager, SF automatic scanner; and, FIG. 14 is a laser printed reproduction of the signal intensities of oligonucleotide probes pre-treated with 1.0 M sodium hydroxide (NaOH) in 10 millimolar ethylenediaminetetra-acetic acid (EDTA) in 0.01% sodium dodecyl sulfate (SDS), and hybridized with $^{32}$P radiolabeled, 109 base pair polymerase chain reaction (PCR) targets, and compared to a standard control, non-pre-treated strip, with detection via a PhosphorImager, SF automatic scanner.

FIG. 13 is a laser printed reproduction of the signal intensities of oligonucleotide probes pre-treated with 1.0 M (Molar) sodium hydroxide (NaOH) in 10 millimolar ethylenediaminetetra-acetic acid (EDTA), in 0.01% sodium dodecyl sulfate (SDS), and hybridized with $^{32}P$ radiolabeled, synthetic A-902 oligonucleotide targets, as compared to a standard control, non-pre-treated strip. Detection was made via a PhosphorImager, SF automatic scanner.

The increased hybridization signal intensities for the pre-treated probes, as compared to the signal intensity of the standard control, non-pre-treated probe are set forth in Table 10 below

TABLE 10

| Control/ Pre-Treated With 1.0M (Molar) NaOH in Solution | Average Mean Signal Intensity (Visible Bands) | Ratio of Average Mean Signal Intensity (Visible Bands) of the Pre-Treated Probes to the Control |
| --- | --- | --- |
| Control | 15,879 | — |
| 1.0M NaOH | 15,8860 | 10 |

EXAMPLE 11

Improvement in signal intensity was demonstrated when polymerase chain reaction (PCR) target biomolecules were initially labeled with a radiolabel. Oligonucleotide probes were pre-treated with 1.0M sodium hydroxide (NaOH), in 10 millimolar ethylenediaminetetra-acetic acid (EDTA), in 0.01% sodium dodecyl sulfate (SDS), for about 5 minutes at about 22 degrees C. The pre-treated probes were rinsed with a fresh amount of sodium saline citrate buffer for three separate 5 minute time periods to remove excess pre-treatment solution. The pre-treated probes were hybridized with complementary 5' $^{32}$P radiolabeled 109 base pair polymerase chain reaction (PCR) targets.

Figure 14:
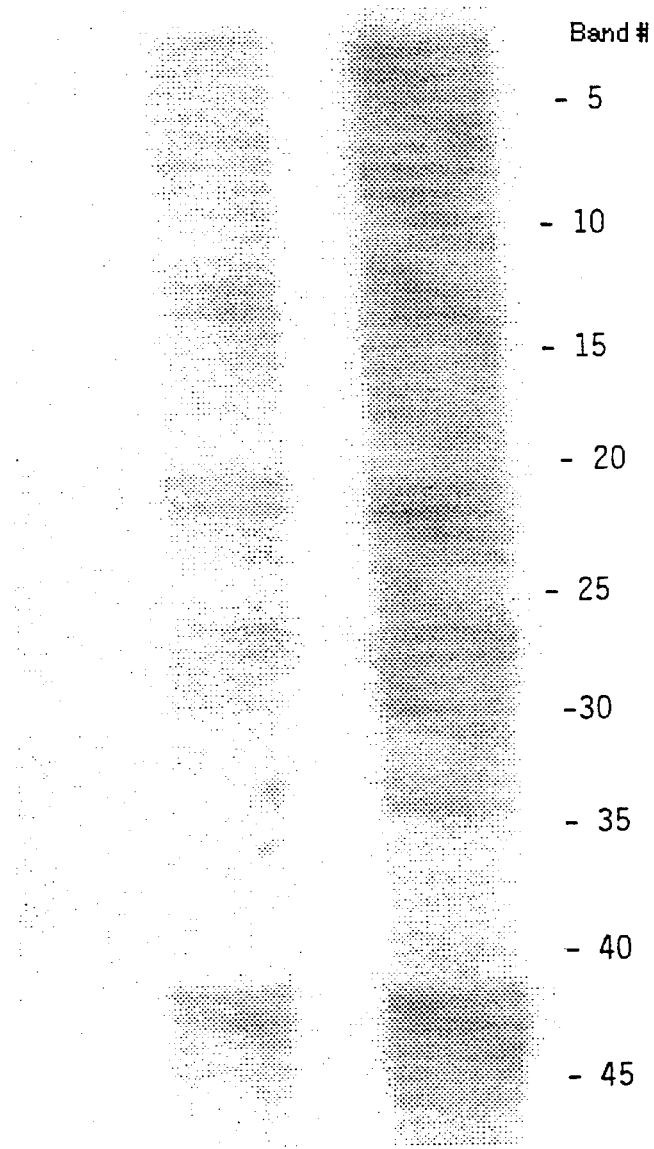

FIG. 14 is a laser printed reproduction of the signal intensities of oligonucleotide probes pre-treated with 1.0 M (Molar) sodium hydroxide (NaOH) in 10 millimolar ethylenediaminetetra-acetic acid (EDTA), in 0.01% sodium dodecyl sulfate (SDS), and hybridized with $^{32}$P radiolabeled, 109 base pair polymerase chain reaction (PCR) targets, as compared to a standard control, non-pre-treated strip. Detection was made via a PhosphorImager, SF automatic scanner.

The increased hybridization signal intensity for the pre-treated probes, as compared to the signal intensity of the standard control, non-pre-treated probe is set forth in Table 11 below.

TABLE 11

| Control/<br>Pre-Treated With<br>1.0M (Molar)<br>NaOH in<br>Solution | Average Mean<br>Signal Intensity<br>(Visible Bands) | Ratio of Average Mean Signal<br>Intensity (Visible Bands) of the Pre-<br>Treated Probes to the Control |
|---|---|---|
| Control | 1661 | — |
| 1.0M NaOH | 17,972 | 10.8 |

Although the present invention has been described in considerable detail with reference to certain preferred versions thereof, other versions are possible. It is intended to cover all modifications, alternatives and equivalents which may fall within the spirit and scope of the invention as defined in the appended claims.

What is claimed is:

1. An improved method for detecting hybridized biomolecules comprising the steps of a) providing a plurality of single stranded probe biomolecules on a solid support surface;

b) pre-treating the plurality of single stranded probe biomolecules with an effective amount of a pre-treatment solution to produce a signal having an increased intensity of at least two (2) times, as compared to an identical detection method that does not include the pre-treating step;

c) applying a buffer solution to the single stranded probe biomolecules;

d) hybridizing the single stranded probe biomolecules with a plurality of target biomolecules wherein the target biomolecules are in solution, to form a hybridized complex; and, e) developing and detecting the signal intensity.

2. The method of claim 1 wherein the developing step includes the steps of:

treating the hybridized complex with a conjugating solution; and, treating the conjugated hybridized complex with a detection reagent.

3. The method of claim 1 wherein the probe biomolecule is a material selected from the group consisting of deoxyribonucleic acid, ribonucleic acid, and peptide-nucleic acid.

4. The method of claim 1 wherein the solid support surface comprises polypropylene.

5. The method of claim 1 wherein the target biomolecule is a material selected from the group consisting of deoxyribonucleic acid, ribonucleic acid, peptide-nucleic acid, and polymerase chain reaction fragments.

6. The method of claim 1 wherein the pre-treatment solution is a solution comprising a denaturant selected from the group consisting of dimethyl formamide, formamide, urea, guanidinium hydrochloride, guanidinium thiocyanate, guanidinium isocyanate, spermine, spermidine, glyoxal, alcohols, and 1,1,3,3-tetramethyl urea.

7. The method of claim 6 wherein the solution of the denaturant further comprises sodium dodecyl sulfate, ethylenediaminetetra-acetic acid, or a mixture thereof.

8. The method of claim 1 wherein the pre-treatment solution is a solution comprising an organic acid selected from the group consisting of acetic acid, formic acid, trifluoroaacetic acid, and trichloroacetic acid.

9. The method of claim 1 wherein the pre-treatment solution is an aqueous solution comprising a base selected from the group consisting of sodium hydroxide, lithium hydroxide, sodium carbonate, sodium bicarbonate, and methyl mercuric hydroxide.

10. The method of claim 9 wherein the aqueous solution of the base further comprises sodium dodecyl sulfate, ethylenediaminetetra-acetic acid, or a mixture thereof.

11. The method of claim 9 wherein the aqueous solution of base comprises sodium hydroxide having a concentration of 10 molar or less.

12. The method of claim 11 wherein the aqueous solution of base comprising sodium hydroxide having a concentration of 10 molar or less further comprises 10 millimolar ethylenediamenetetra-acetic acid and 0.01% sodium dodecyl sulfate.

13. The method of claim 1 wherein the pre-treatment solution is an aqueous solution comprising a salt selected from the group consisting of sodium chloride, potassium chloride, lithium chloride, sodium acetate, sodium citrate, sodium phosphate, magnesium chloride, manganese chloride, cesium chloride, barium chloride, and sodium dodecyl sulfate.

14. The method of claim 1 wherein the pre-treatment solution is an aqueous solution comprising hydrochloric acid having a concentration of less than 1 Normal.

15. The method of claim 1 wherein the pre-treating step is carried out at a temperature in the range of about 20 degrees C. to about 30 degrees C., and for an effective period of time in the range of about 1 minute to about 60 minutes.

16. In a reverse Southern blot method for detecting hybridized biomolecules comprising the steps of:

a) providing a plurality of single stranded probe biomolecules on a solid support surface;

b) applying a buffer solution to the single stranded probe biomolecules;

c) hybridizing the single stranded probe biomolecules with a plurality of target biomolecules to form a hybridized complex; and, d) developing and detecting a signal intensity;

the improvement comprising before the step of applying the buffer, the step of:

e) pre-treating the plurality of single stranded probe biomolecules with an effective amount of a pre-treatment solution that increases the signal intensity by at least two (2) times, as compared to an identical detection method that does not include the pre-treating step.

17. An improved method for hybridization detection comprising the steps of:

a) providing a plurality of single stranded deoxyribonucleic acid probes on a solid polypropylene support surface;

b) pre-treating the plurality of single stranded probes with an effective amount of a pre-treatment solution, at a temperature in the range of about 20 degrees C. to about 30 degrees C., and for an effective period of time in the range of about 1 minute to about 60 minutes, to produce a signal having an increased intensity of at least two (2) times, as compared to an identical detection method that does not include the pre-treating step;

c) applying a buffer solution to the plurality of single stranded probes;

d) hybridizing the single stranded probes with a plurality of target biomolecules selected from the group consisting of deoxyribonucleic acid and polymerase chain reaction fragments, wherein the target biomolecules are in solution, to form a hybridized complex; and, e) developing and detecting the signal intensity.

18. The method of claim 17 wherein the developing step includes the steps of:

treating the hybridized complex with a conjugating solution; and, treating the conjugated, hybridized complex with a detection reagent.

19. The method of claim 17 wherein the pre-treatment solution is a solution comprising a denaturant selected from the group consisting of dimethyl formamide, formamide, urea, guanidinium hydrochloride, guanidinium thiocyanate, guanidinium isocyanate, spermine, spermidine, glyoxal, alcohols, and 1,1,3,3-tetramethyl urea.

20. The method of claim 17 wherein the pre-treatment solution is a solution comprising an organic acid selected from the group consisting of acetic acid, formic acid, trifluoroacetic acid, and trichloroacetic acid.

21. The method of claim 17 wherein the pre-treatment solution is an aqueous solution comprising a base selected from the group consisting of sodium hydroxide, lithium hydroxide, sodium carbonate, sodium bicarbonate, and methyl mercuric hydroxide.

22. The method of claim 17 wherein the pre-treatment solution is an aqueous solution comprising a salt selected from the group consisting of sodium chloride, potassium chloride, lithium chloride, sodium acetate, sodium citrate, sodium phosphate, magnesium chloride, manganese chloride, cesium chloride, barium chloride, and sodium dodecyl sulfate.

23. The method of claim 17 wherein the pre-treatment solution is an aqueous solution comprising hydrochloric acid having a concentration of less than 1 Normal.

24. An improved reverse Southern blot method for detecting hybridized biomolecules comprising the steps of:
   a) providing a plurality of single stranded probe biomolecules on a solid support surface;
   b) pre-treating the plurality of single stranded probe biomolecules with an effective amount of hot water having a temperature in the range of about 90 degrees C. to about 97 degrees C., and pre-treating the plurality of single stranded probe biomolecules for an effective period of time in the range of about 30 seconds to about 45 minutes, to produce a signal having an increased intensity of at least two (2) times, as compared to an identical detection method that does not include the pre-treating step;
   c) applying a buffer solution to the single stranded probe biomolecules;
   d) hybridizing the single stranded probe biomolecules with a plurality of target biomolecules wherein the target biomolecules are in solution, to form a hybridized complex; and,
   e) developing and detecting the signal intensity.

25. The method of claim 24 wherein the developing step includes the steps of:
   treating the hybridized complex with a conjugating solution; and,
   treating the conjugated, hybridized complex with a detection reagent.

26. A kit for detecting hybridized biomolecules comprising:
   a) a plurality of single stranded probe biomolecules on a solid polypropylene support surface;
   b) an effective amount of a pre-treatment solution for application to the single stranded probe biomolecules to produce a signal of interest having an increased intensity of at least two (2) times, as compared to probe biomolecules that are not pre-treated with the pre-treatment solution;
   c) a buffer solution;
   d) a plurality of target biomolecules for hybridization with the single stranded probe biomolecules to form a hybridized complex;
   e) a conjugating solution for developing the signal of interest; and,
   f) a detection reagent for detecting the signal of interest.

* * * * *

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:   synthetic
      oligonucleotide

<400> SEQUENCE: 1
acaccgccgg                                                          10

<210> SEQ ID NO 2
<211> LENGTH: 63
<212> TYPE: DNA
<213> ORGANISM: Artificial Sequence
<220> FEATURE:
<223> OTHER INFORMATION: Description of Artificial Sequence:   synthetic
      oligonucleotide

<400> SEQUENCE: 2
tggatggtca gcgcactctt gcccacaccg ccggcgccca ccaccaccag cttatattcc    60
gtc                                                                 63

<210> SEQ ID NO 3
<211> LENGTH: 109
<212> TYPE: DNA
<213> ORGANISM: Artificial Sequence
<220> FEATURE:
<223> OTHER INFORMATION: Description of Artificial Sequence:   synthetic
      oligonucleotide

<400> SEQUENCE: 3
ctctatagtg gggtcgtatt cgtccacaaa atggttctgg atcagctgga tggtcagcgc    60
actcttgccc acaccgccgg cgcccaccac caccagctta tattccgtc              109